US005802494A

United States Patent [19]
Kuno

[11] Patent Number: 5,802,494
[45] Date of Patent: *Sep. 1, 1998

[54] PATIENT MONITORING SYSTEM

[75] Inventor: Yoshinori Kuno, Kawasaki, Japan

[73] Assignee: Kabushiki Kaisha Toshiba, Kawasaki, Japan

[*] Notice: This patent issued on a continued prosecution application filed under 37 CFR 1.53(d), and is subject to the twenty year patent term provisions of 35 U.S.C. 154(a)(2).

[21] Appl. No.: 692,431

[22] Filed: Aug. 5, 1996

Related U.S. Application Data

[63] Continuation of Ser. No. 390,816, Feb. 16, 1995, abandoned, which is a continuation of Ser. No. 729,178, Jul. 12, 1991, abandoned.

[30] Foreign Application Priority Data

Jul. 13, 1990 [JP] Japan ................................. 2-184004

[51] Int. Cl.$^6$ ................................................ G06F 159/00
[52] U.S. Cl. ................................................ 705/2; 128/920
[58] Field of Search .......................... 395/93, 94, 84, 395/88; 318/568.25; 358/108, 136, 209; 381/43, 53; 128/660.02, 660.03, 660.07, 904, 903, 653.1, 774, 782, 922, 920; 382/128, 118

[56] References Cited

U.S. PATENT DOCUMENTS

| | | | |
|---|---|---|---|
| 3,767,859 | 10/1973 | Doering et al. | 179/1 |
| 3,805,238 | 4/1974 | Rothfjell | 382/118 |
| 3,946,159 | 3/1976 | Fay . | |
| 4,045,815 | 8/1977 | Griffith et al. | 358/183 |
| 4,051,522 | 9/1977 | Healy et al. | 358/86 |
| 4,449,189 | 5/1984 | Feix et al. | 382/118 |
| 4,769,845 | 9/1988 | Nakamura | 381/43 |
| 4,847,688 | 7/1989 | Nishimura et al. . | |
| 4,933,873 | 6/1990 | Kaufman et al. | 364/413.02 |
| 4,975,969 | 12/1990 | Tal | 382/2 |
| 4,992,866 | 2/1991 | Morgan . | |
| 5,008,946 | 4/1991 | Ando | 382/2 |
| 5,012,522 | 4/1991 | Lambert | 382/118 |
| 5,083,201 | 1/1992 | Ohba | 382/118 |
| 5,086,480 | 2/1992 | Sexton | 382/118 |
| 5,410,609 | 4/1995 | Kado et al. | 382/118 |

FOREIGN PATENT DOCUMENTS

| | | |
|---|---|---|
| 0420 657 | 4/1991 | European Pat. Off. . |
| 0467 094 | 1/1992 | European Pat. Off. . |
| 2 142 500 | 1/1985 | United Kingdom . |

OTHER PUBLICATIONS

Proceedings of the 1987 IEEE International Conference on Systems, Man, and Cybernatics, vol. 3 3/3, Oct. 20,1987, pp. 970–974, Kenji Mase, et al., "Head Reader—A Head Motion Understanding System For Better Man–Machine Interaction".

NNT Review, vol. 1, No. 2, Jul. 1989, pp.68–72, Yashuhisa Ikeda, "Scope Port D64 Image Monitoring System Via the Ins–Net".

Primary Examiner—Ayaz R. Sheikh
Assistant Examiner—Xuonk M. Chunk-Trans
Attorney, Agent, or Firm—Oblon, Spivak, McClelland, Maier & Neustadt, P.C.

[57] ABSTRACT

The patient monitoring system includes a patient-data-acquiring section and a monitor section. The patient data-acquiring section includes a data-inputting device for inputting at least one of two data items, the first data item representing a patient image, and the second data item representing the physical conditions of the patient, a detecting circuit for detecting whether or not it is necessary to examine the patient's image on the basis of the data items input by the data-inputting device, a message-sending device for sending a message to the patient asking whether or not the patient agrees to be examined when the detecting circuit detects that it is necessary to examine the subject's image, an agreement-recognizing circuit for recognizing the patients's agreement to being examined, and a data-transmitting circuit for transmitting the first data item to a monitor room when the agreement-recognizing means recognizes the patient's agreement. The monitor section includes a display for displaying the patients's image represented by the first data item transmitted by the data-transmitting circuit.

18 Claims, 23 Drawing Sheets

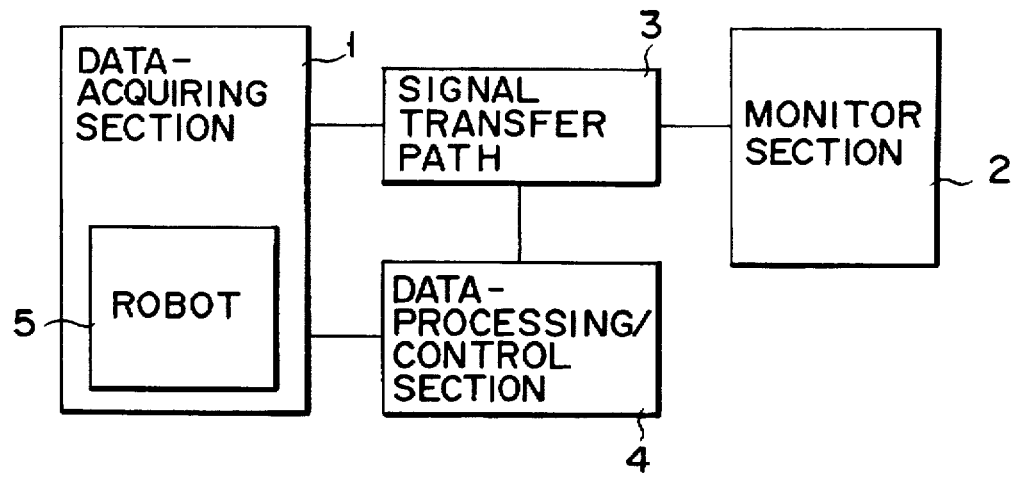
F I G. 1
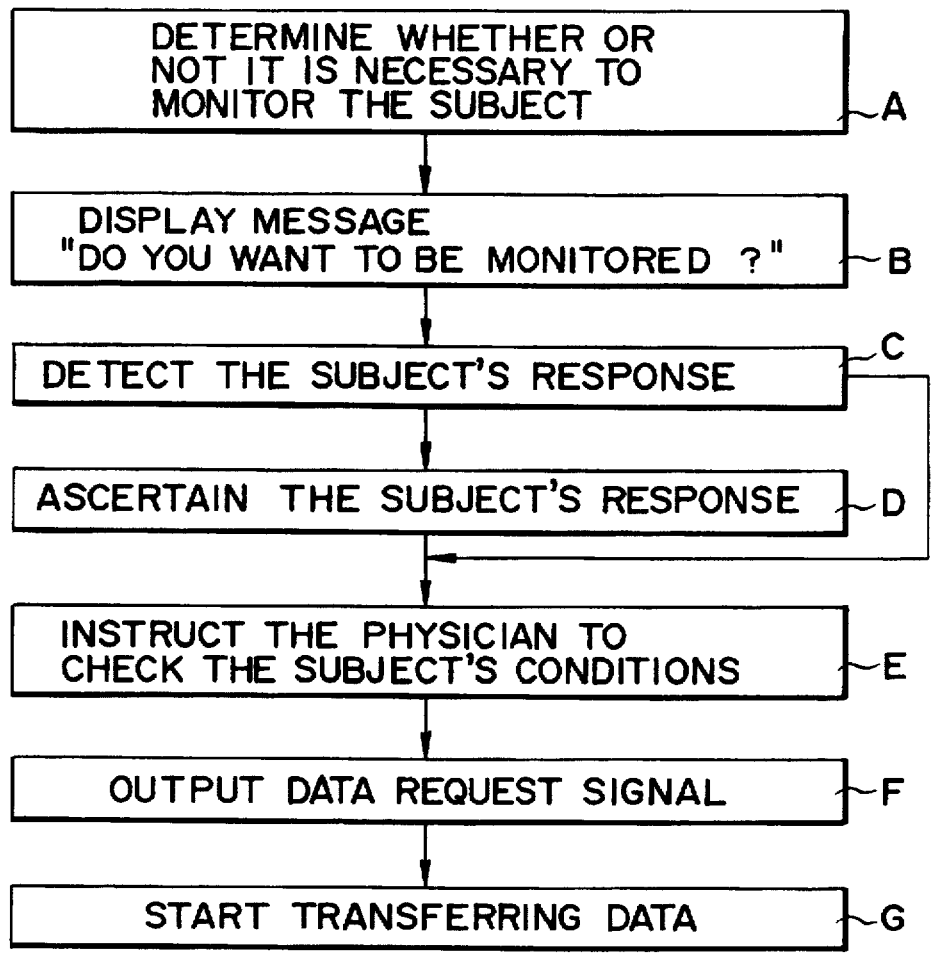
F I G. 2A

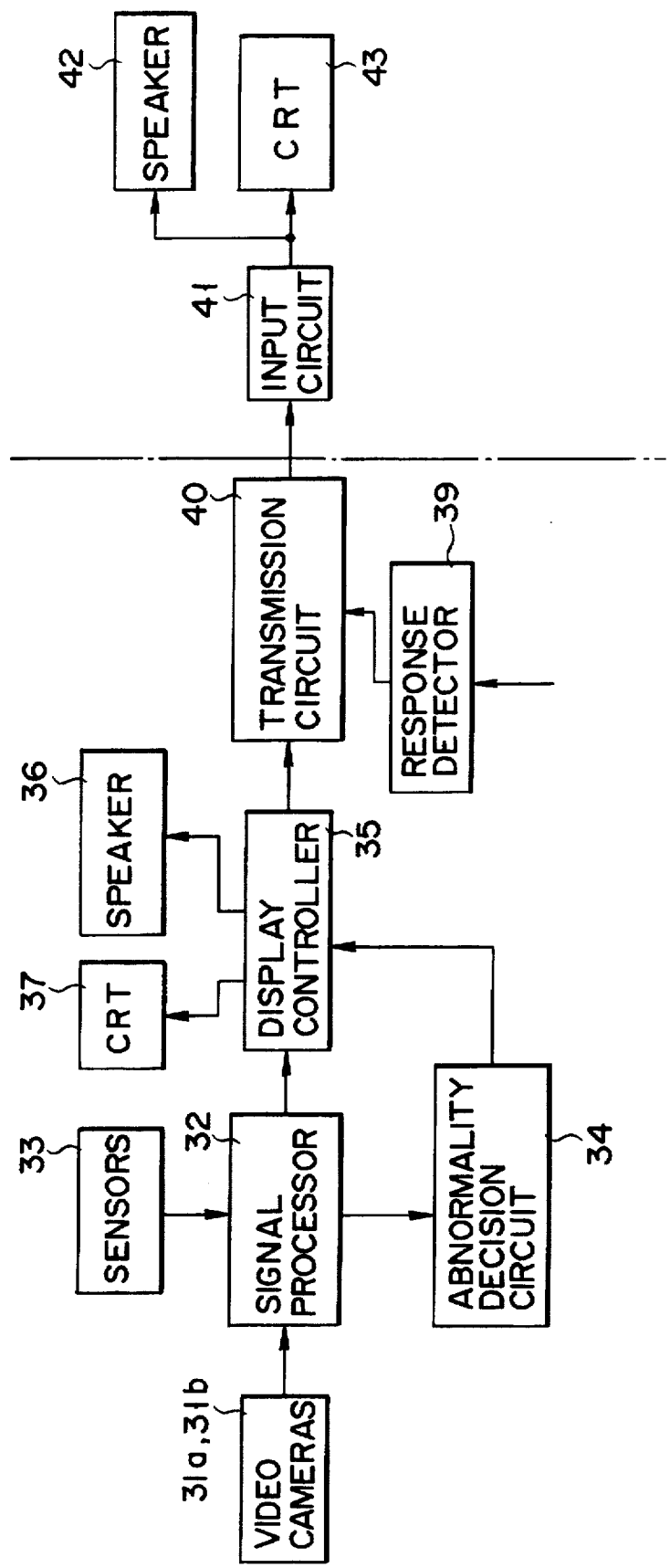
F I G. 2B

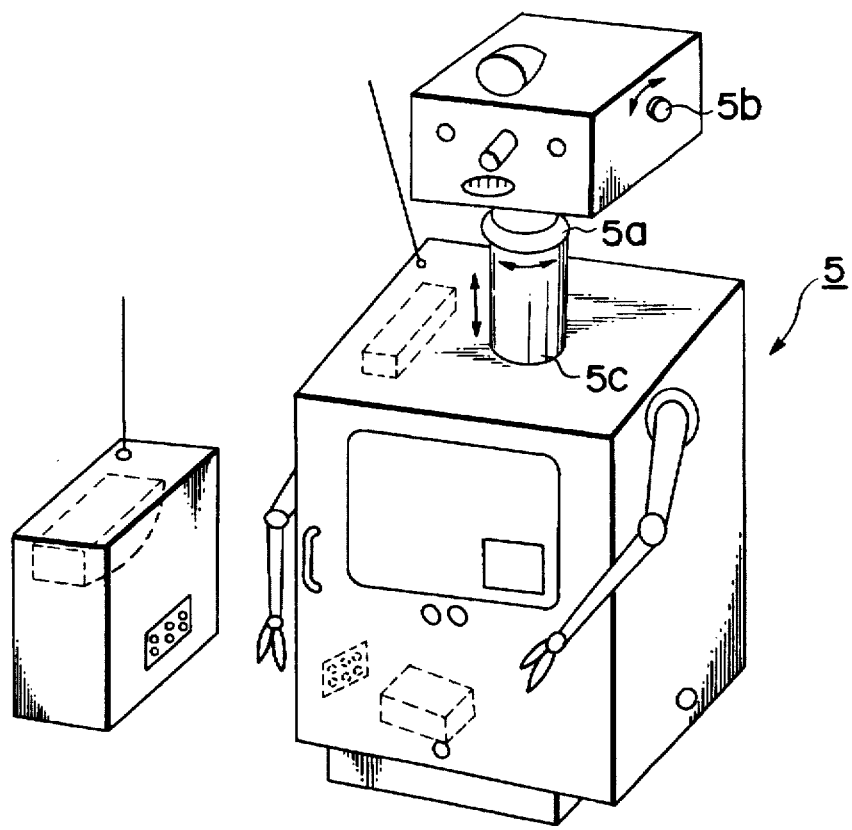
F I G. 4
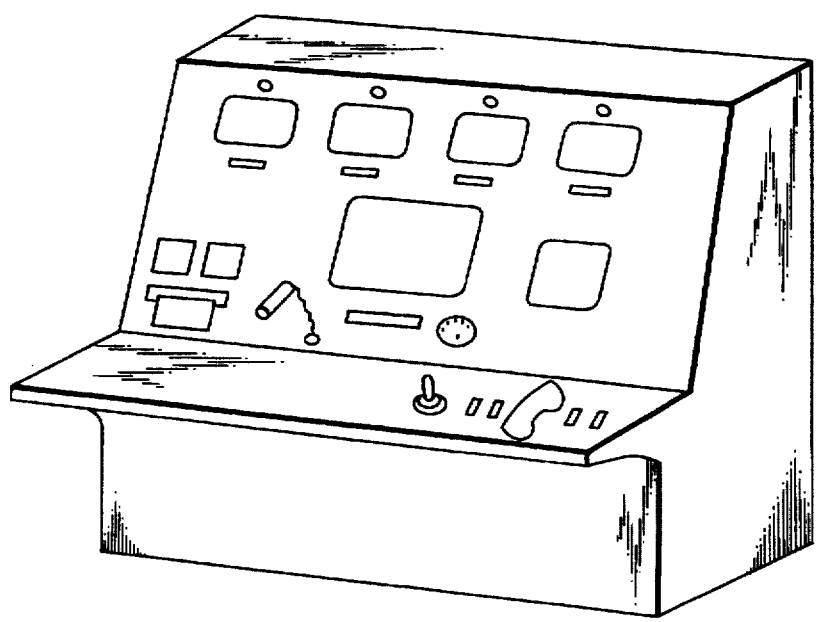
F I G. 5

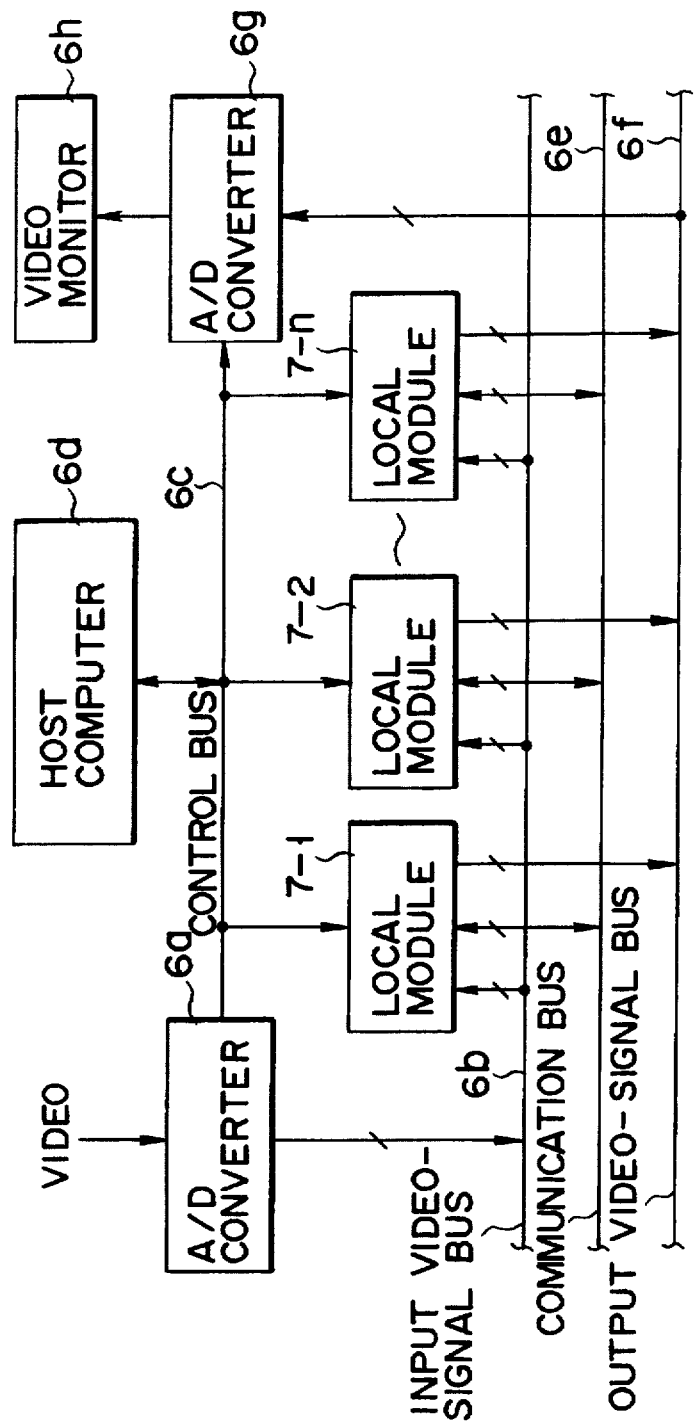
F I G. 6

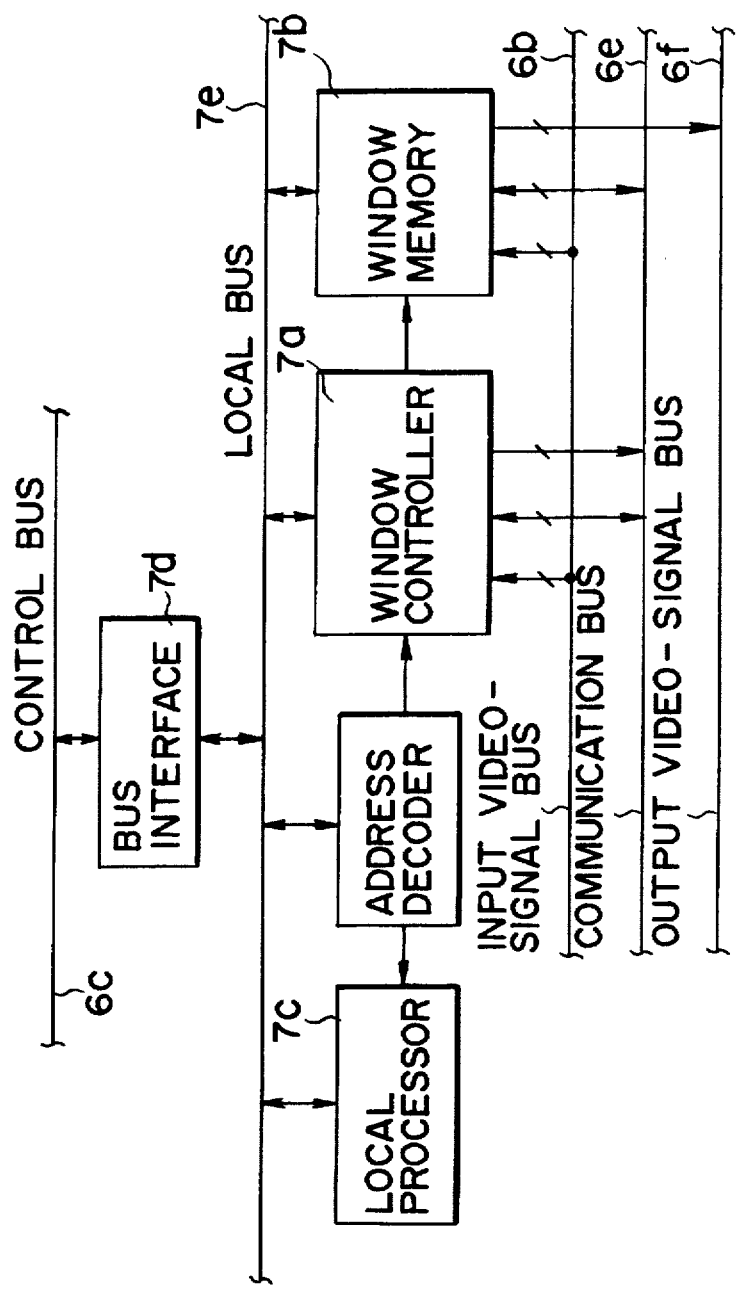
F I G. 7

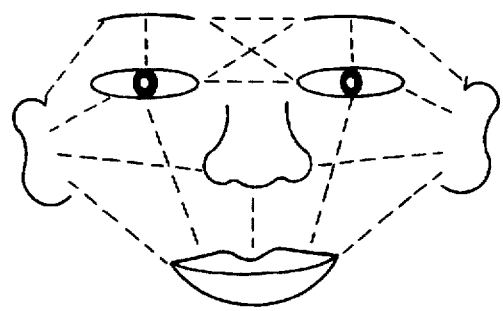
F I G. 16
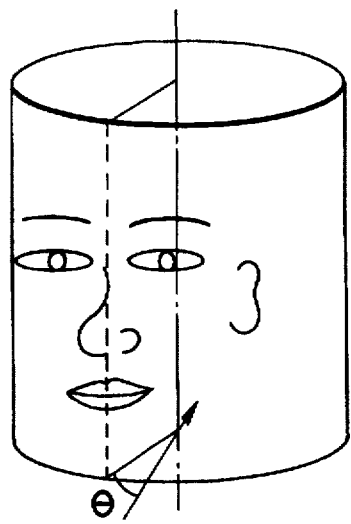 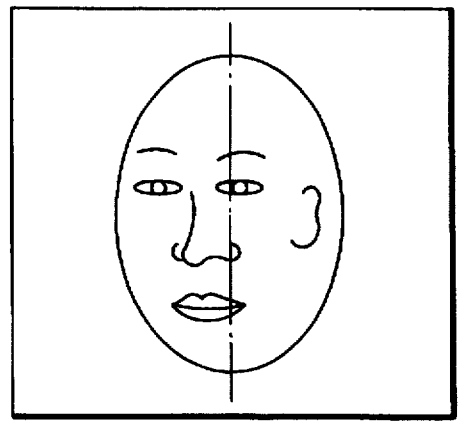
F I G. 17A    F I G. 17B
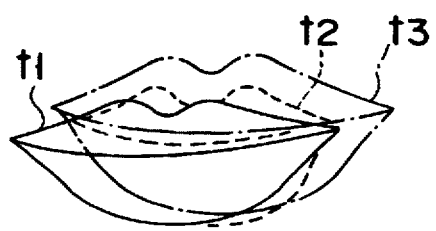
F I G. 18

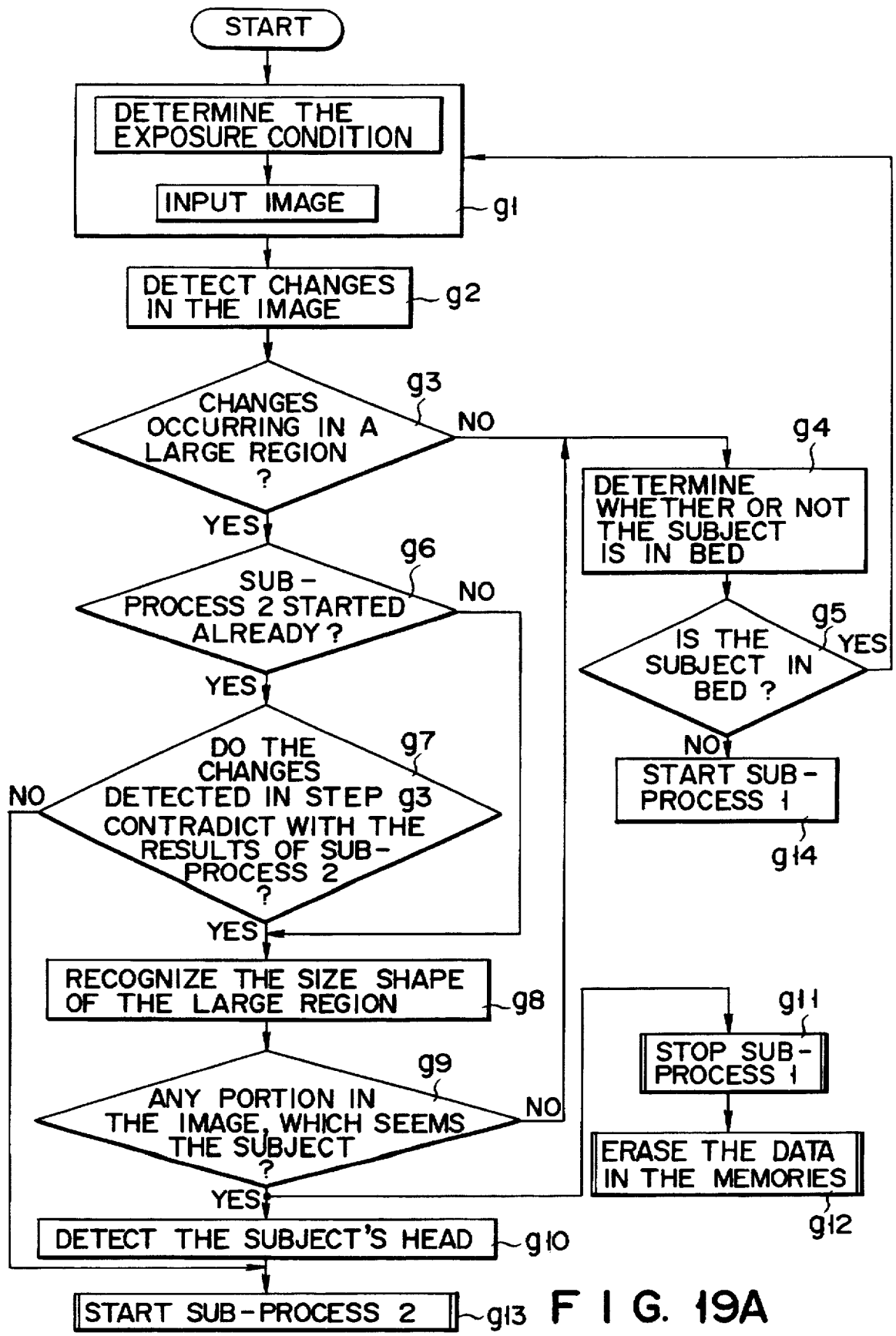
F I G. 19A

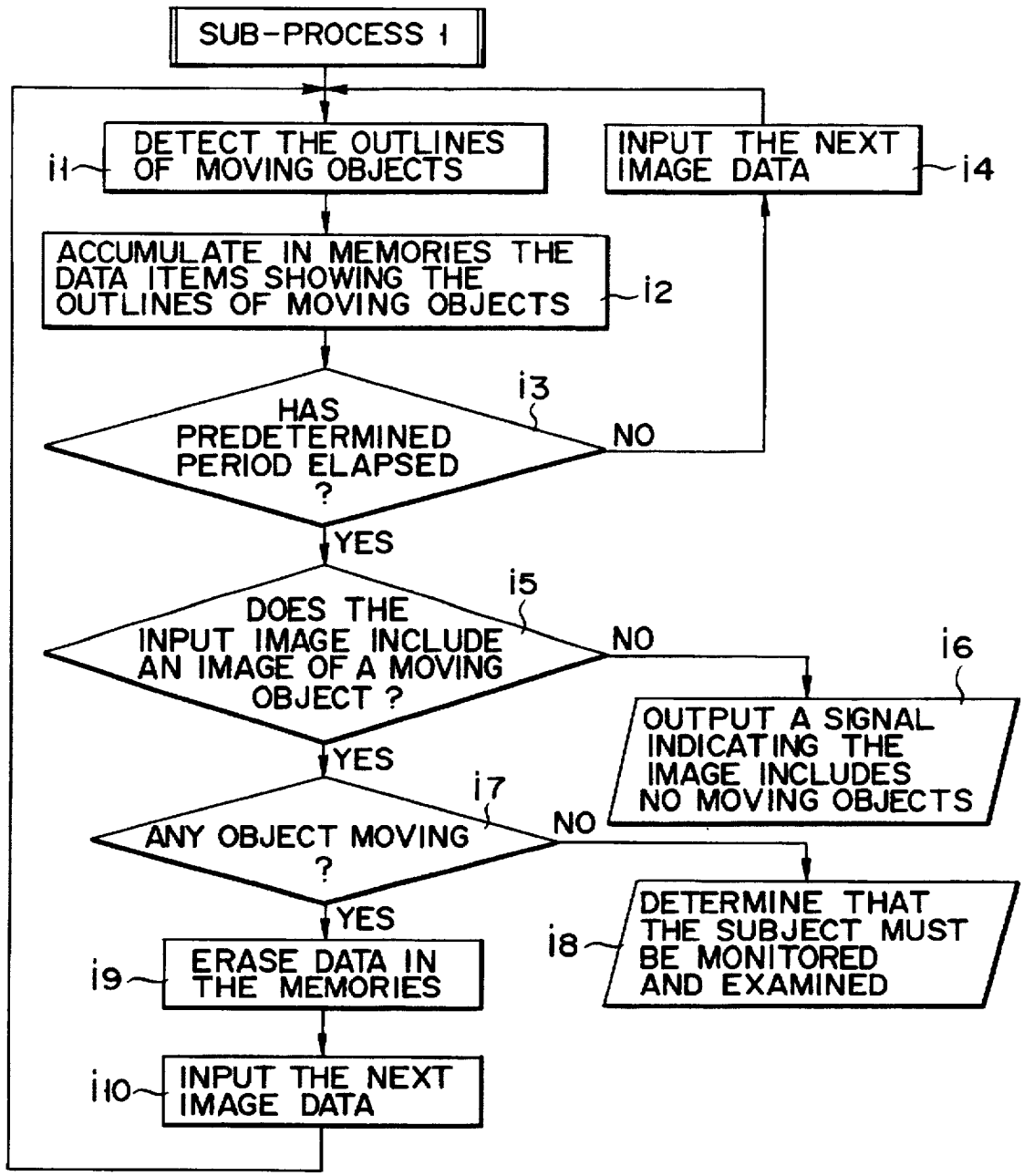
F I G. 19B

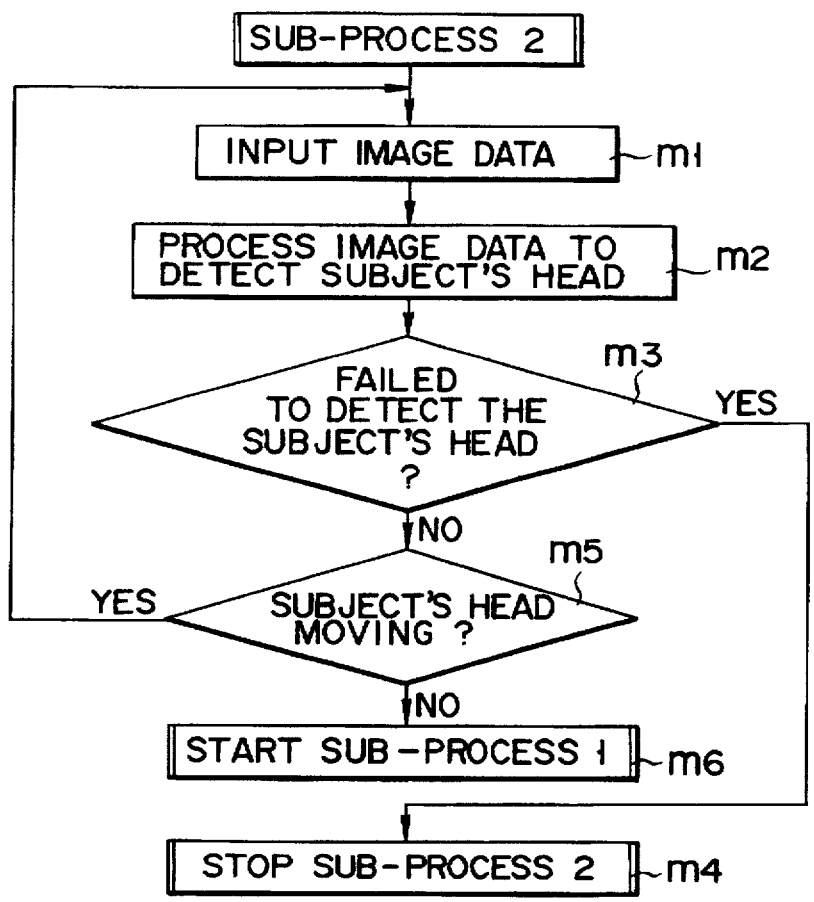
F I G. 19C
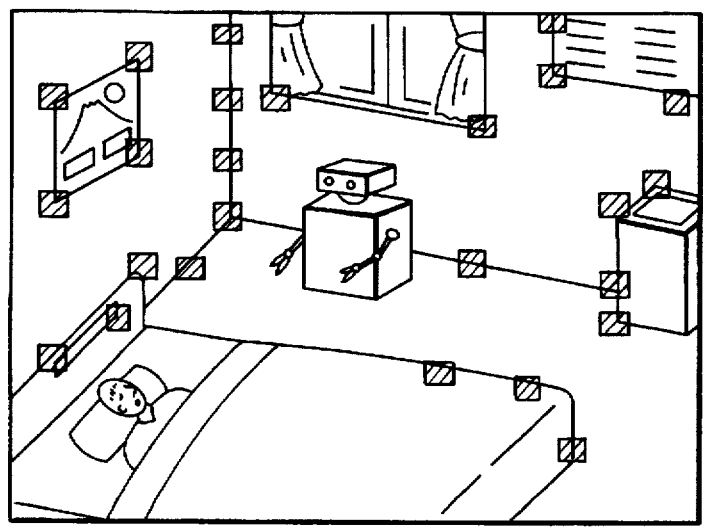
F I G. 20

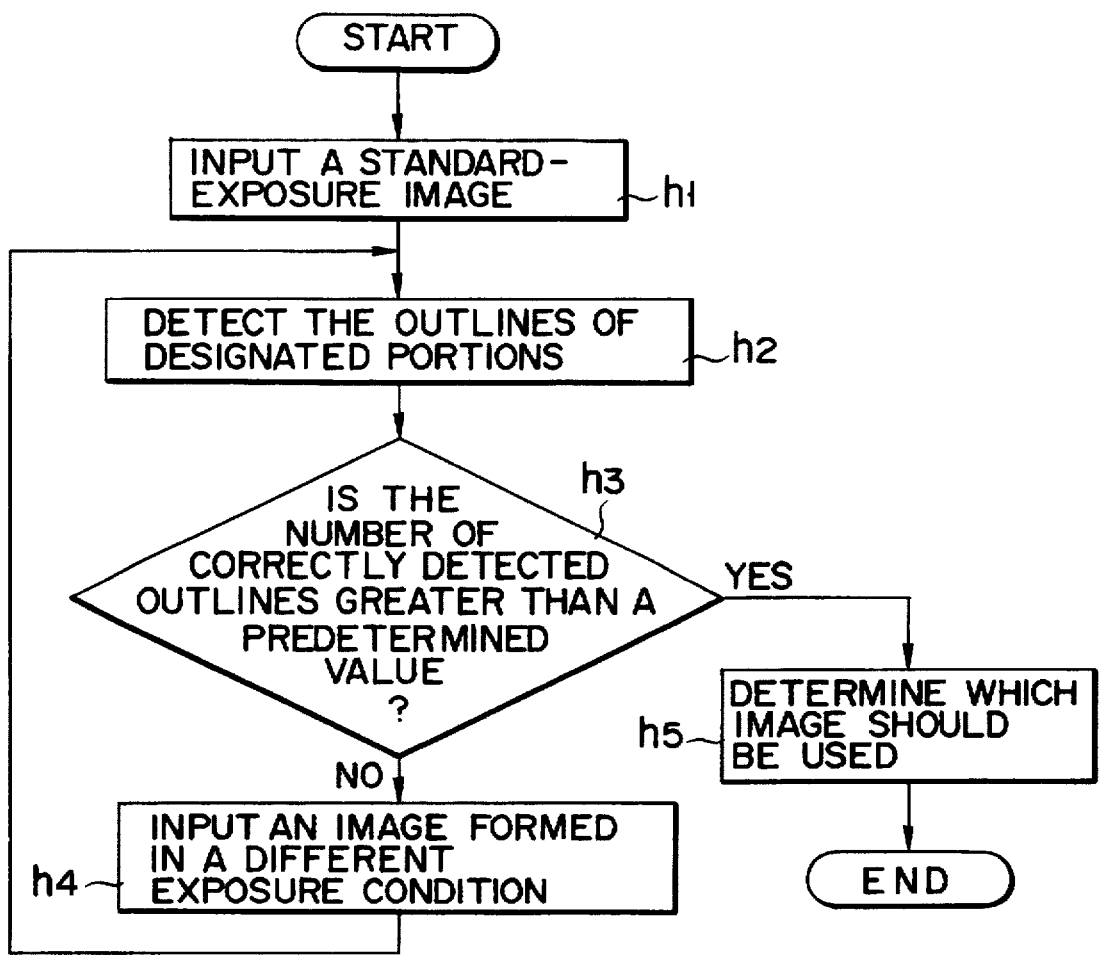
F I G. 21

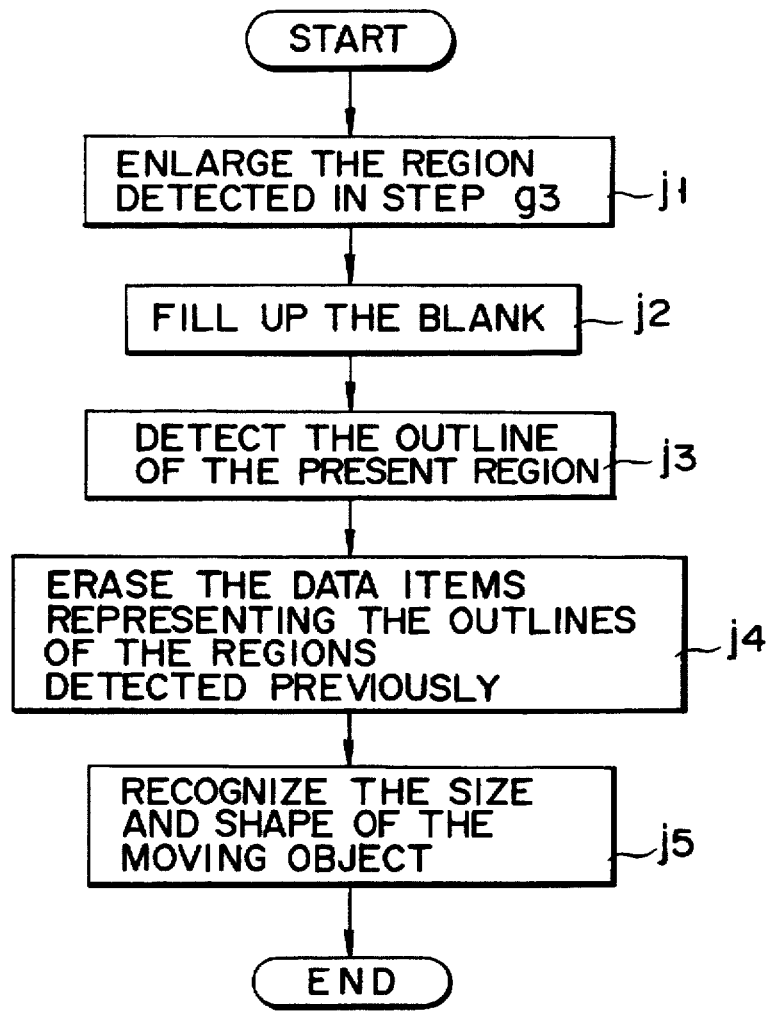
F I G. 23

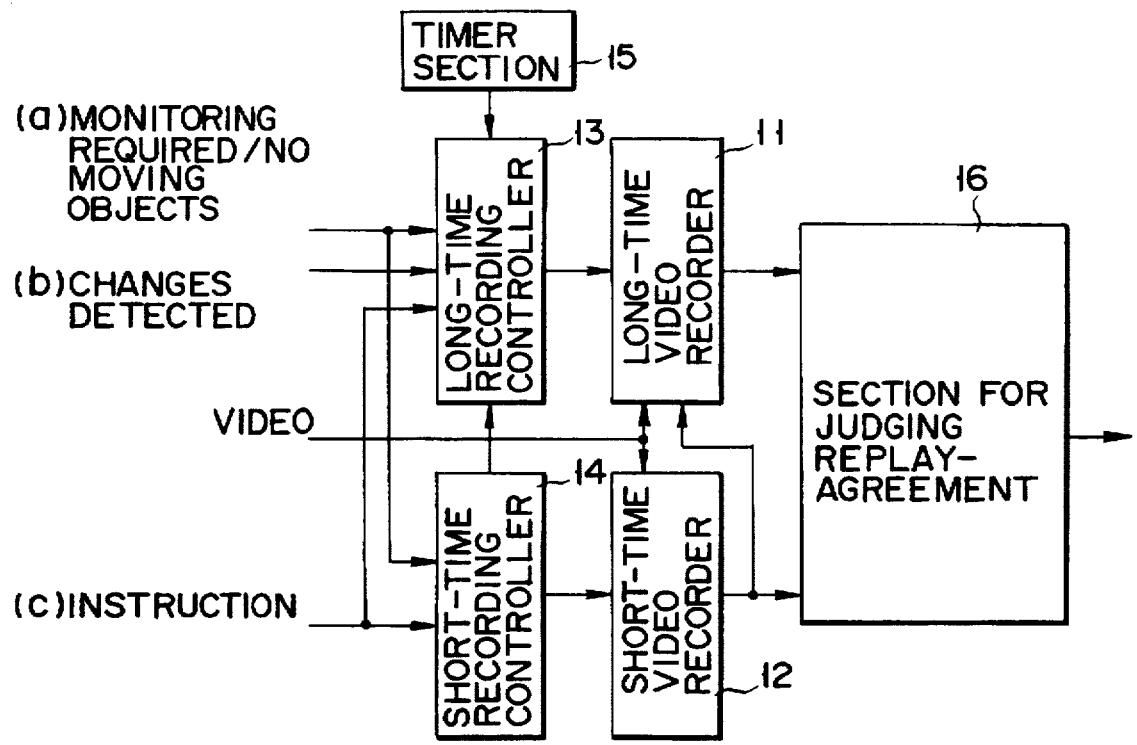
F I G. 26
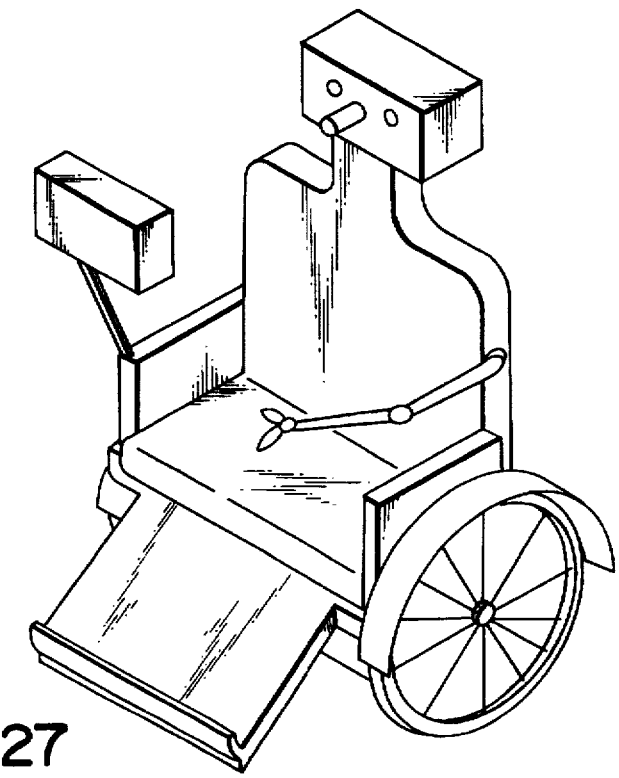
F I G. 27

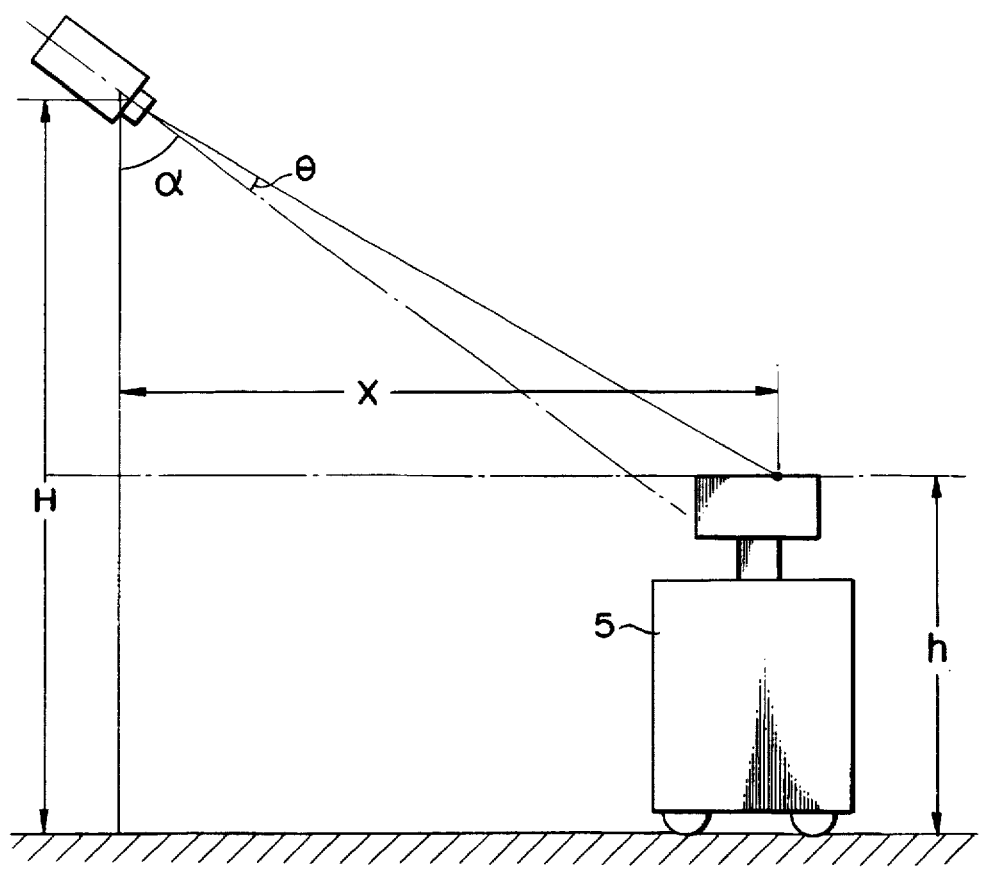
F I G. 28
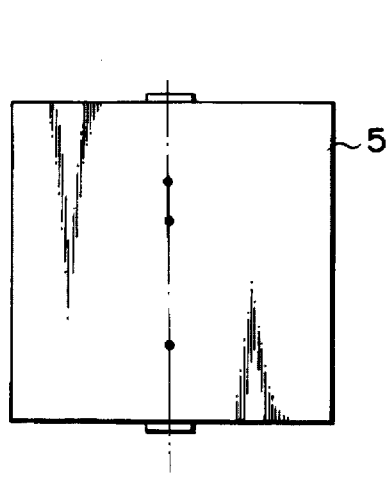
F I G. 29
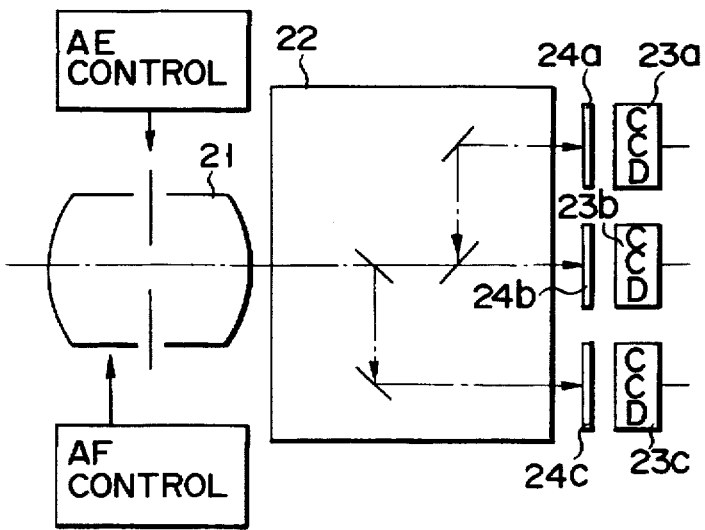
F I G. 30

5,802,494

PATIENT MONITORING SYSTEM

This application is a Continuation of application Ser. No. 08/390,816, filed on Feb. 16, 1995, now abandoned, which is a CON of Ser. No. 07/729,178 filed on Jul. 12, 1991, now abandoned.

BACKGROUND OF THE INVENTION

1. Field of the Invention

The present invention relates to a system for monitoring a subject effectively, which comprises a video camera for taking a picture of the subject and a CRT display for displaying an image of the subject.

2. Description of the Related Art

A system has been developed which monitors a patient in bed or an elderly person sick in bed. The system comprises a video camera set in the sickroom and a CRT display installed in a monitor room such as a nurse station. The video camera takes pictures of the subject. The signals output by the video camera and representing the image of the subject are supplied via a cable to the CRT display. The CRT display displays the image of the subject, whereby a physician in the monitor room can observe the subject.

The monitor system further comprises electronic diagnosing devices, such as an electronic hemadynamometer and an electrocardiograph, attached to the subject. These diagnosing devices detect the physical conditions of the subject, e.g., the blood pressure and the number of pulses per unit time. The data items output by these devices and representing the physical conditions of the subject are supplied via the cable to the monitor room. Thus, a physician in the monitor room can read the blood pressure of the subject, examine the electrocardiogram of the subject, and check other physical conditions of the subject, while observing the subject on the screen of the CRT display.

The monitor system enables a physician in the monitor room to observe simultaneously two or more subjects who are in different rooms. The system of this type, however, is disadvantageous in two respects. First, to achieve perfect observation of the subject, the physician in the monitor room must keep watching the CRT display screen, which is a great burden. Second, the subject cannot help but be conscious of being watched at all times and of his or her privacy being invaded, and inevitably suffers from great mental stress.

SUMMARY OF THE INVENTION

The object of the present invention is to provide a monitor system for observing a subject only when necessary and proper, so that a physician is relieved from the burden of continuously watching a monitor CRT display, and the subject needs not have his or her privacy invaded at all.

In an aspect, the present invention provides a monitor system, wherein the image of a subject, taken by a video camera set in the sickroom or bedroom, is analyzed by analysis means installed in the sickroom or bed room, it is determined from the results of the analysis whether or not it is necessary to monitor the subject, the subject is informed of whether or not he or she needs to be monitored, and the signals showing the subject's image are transmitted to a CRT display installed in a monitor room, only if the subject must be monitored and if the subject agrees to be monitored, whereby a physician can monitor the subject.

Thus, the physician can observe the subject only when necessary and given permission by the subject, and is relieved from the great burden which the physician must bear otherwise. Since the subject is monitored only when necessary and only if he or she agrees to be monitored, he or she does not have his or her privacy invaded, and hence does not suffer from mental stress.

BRIEF DESCRIPTION OF THE DRAWINGS

FIG. 1 is a block diagram schematically showing a monitor system according to the present invention;

FIG. 2A is a flow chart illustrating the operation of the system shown in FIG. 1;

FIG. 2B is a block diagram showing the monitor system in greater detail;

FIG. 4 is a perspective view showing the robot located in the sickroom or bedroom;

FIG. 5 is a perspective view of the equipment installed in a monitor room;

FIG. 6 is a block diagram representing the image-processing apparatus incorporated in the monitor system;

FIG. 7 is a block diagram showing the local module used in the image-processing apparatus of FIG. 6;

FIG. 16 is also a diagram showing the position relationship among the eyebrows, eyes, ears, nose and mouth of the subject;

FIGS. 17A and 17B are diagrams showing the angle by which the subject faces away from a video camera, and the positions of the subject's eyebrows, eyes, ears, nose and mouth;

FIG. 18 is a diagram explaining the writing into a memory the data items representing the positions which the subject's lips take at different times, so that the data items may be processed to determine the movement of the lips;

FIGS. 19A, 19B and 19C show a flow chart representing how to process the image data a fixed camera has output;

FIG. 20 is a diagram showing the designated portions of the still objects seen in the image input from a fixed video camera installed in the sickroom;

FIG. 21 is a flow chart explaining how to determine the best possible exposure in which the fixed video camera monitor the subject in the sickroom;

FIGS. 23 and 24 are flow charts, each explaining the process of extracting from the image data a part representing an object of interest;

FIG. 26 is a block diagram schematically showing the recording apparatus incorporated in the monitor system (FIG. 1), for recording the image of the subject;

FIG. 27 is a perspective view of a wheelchair robot which can be employed in the monitor system;

FIG. 28 is a diagram illustrating how to determine the position of the robot;

FIG. 29 is a diagram showing marks which are put on the robot; and

FIG. 30 is a diagram schematically showing a camera which can be incorporated in the robot, for simultaneously taking pictures of the subject in different exposure conditions.

DETAILED DESCRIPTION OF THE PREFERRED EMBODIMENTS

Figure 3:
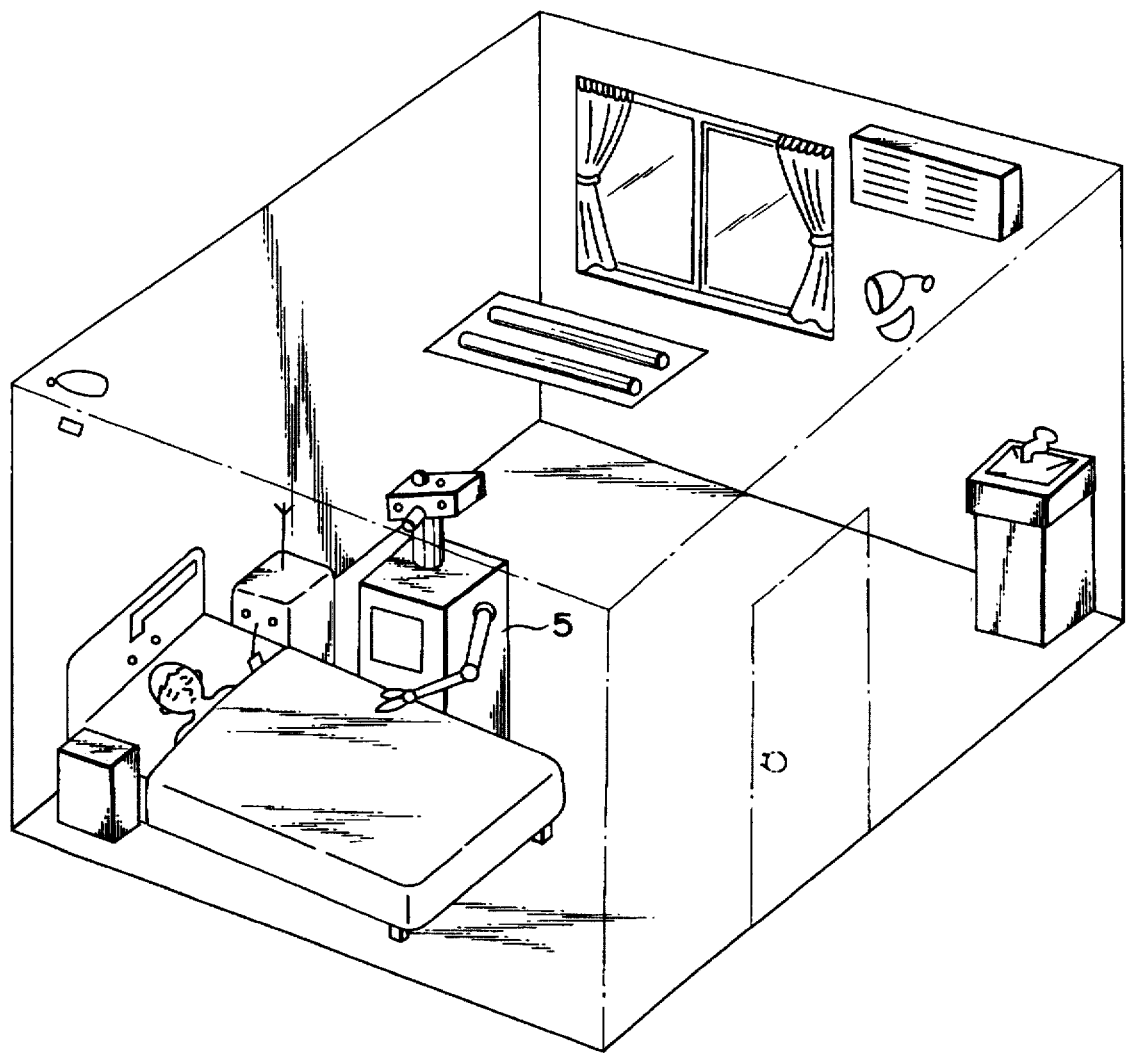
FIG. 3 is a perspective view representing the equipment installed in a sickroom or bedroom.

As is shown in FIG. 1, a monitor system according to the present invention comprises a data-acquiring section 1, a monitor section 2, a signal transfer path 3 connecting the sections 1 and 2 together, and a data-processing/control section 4 connected to the section 1 and the path 3.

As FIG. 3 shows, the data-acquiring section 1 comprises a robot 5, a fixed video camera, an illumination lamp, a speaker, and the like—all installed in a sickroom. If necessary, the section 1 can further comprise electronic diagnosing devices, such as an electronic hemadynamometer and an electrocardiograph, attached to the subject— installed also in the sickroom.

The robot 5 has a video camera in its head, a microphone and a speaker mounted on its head, and a display on its trunk, as is shown in FIG. 4. The video camera takes pictures of the subject sick in bed in the sickroom. The microphone detects any speech the subject utters. The speaker gives the messages to the subject, which a physician makes in the monitor room. The display displays the messages the physician makes. The data-acquiring section 1 further comprises a radio transmitter/receiver, also installed in the sick room. Through this radio transmitter/receiver, control signals are supplied from the monitor section 2 to the robot 5, and various signals are exchanged between the robot 5 and the other components of the section 1, such as the hemadynamometer and the electrocardiograph, both attached to the subject. A wire transmitter/receiver instead of the radio transmitter/receiver may be used for exchanging the signals between the robot 5 and the monitor section 2.

The monitor section 2 comprises a monitor console of the type shown in FIG. 5. The monitor console has several monitor displays for displaying the subject's face represented by the image data transferred from the section 1 via the signal transfer path 3, and also the various physical conditions of the subject represented by the data items transferred from the section 1 via the path 3.

The data-processing/control section 4 is designed to process the various data items the section 1 has acquired of the subject, and controls the sections 1 and 2 in accordance with the results of the data-processing. The section 4, though a component independent of the sections 1 and 2, can be installed in either the sickroom, along with the data-acquiring section 1, or the monitor room, together with the monitor section 2.

The operation of the monitor system shown in FIG. 1 will now be outlined, with reference to the flow chart of FIG. 2A and also with FIG. 2B showing the system in greater detail.

The video camera 31a in the robot 5 and the fixed video camera 31b installed in the sickroom generates video signals representing the image of the subject. Meanwhile, the electronics sensors 33 installed in the sickroom, such as the hemadynamometer and the electrocardiograph, both attached to the subject, output diagnosis signals, representing the physical conditions of the subject. The video signals and the diagnosis signals are input to the signal processor 32 incorporated in the data-processing/control section 4. The processor 32 processes these input signals, thereby generating image data and diagnosis data. The image data and the diagnosis data are supplied to the abnormality decision circuit 34 incorporated in the robot 5. Based on the image data and the diagnosis data the circuit 34 determines, in step A, whether or not it is necessary for a physician to examine and check the subject's facial expression and physical conditions.

If YES in step A, the operation goes to step B. In step B, the abnormality decision circuit 34 supplies an abnormality signal to the display controller 35 built in the robot 5. In response to the abnormality signal, the display controller 35 supplies message data to the speaker 36 and the CRT display 37, both built in the robot 5, whereby the speaker 36 gives a message "DO YOU WANT TO BE MONITORED?", and the CRT display 37 simultaneously displays the same message.

When the subject responds to the message, the response detector 39 incorporated in the data-processing/control section 4 detects the response in step C. The subject's response is the pushing of a response button-switch, an oral response, or a visual response such as nodding, shaking of head, hand signaling, or eye signaling. The button-switch pushing is readily detected by the data-processing/control section 4. The oral response is detected by the speech recognition device incorporated in the data-processing/control section 4. The physical response is detected by the response detector 39. More precisely, the detector 39 detects the physical response from the image data supplied from the video-signal processor built in the section 4 for processing the video signals output by the video cameras 31a and 31b.

If the section 4 detects no response of the subject, either visual or oral, within a predetermined period of time, it determines that the subject agrees that he or she can be monitored.

The most reliable response is the button-switch pushing. Hence, if the subject pushes the response push-button, there is no problem in determining whether or not the subject agrees to be monitored. However, if the subject makes any other type of a response, it remains doubtful as to whether the subject has agreed or not agreed to be monitored. In this case, the operation goes to step D. In step D, the response detector 39 detects the subject's response for the second time in the same way as in step C. Step D is not absolutely necessary, and can therefore be dispensed with.

If YES in step C or step D, that is, if the response detector 39 detects that the subject agrees to be monitored, the operation goes to step E. In step E, the detector 39 supplies a signal to the transmission circuit 40 installed in the sickroom. The transmission circuit 40 transmits the signal to the input circuit 41 incorporated in the monitor section 2. In response to the signal, the input circuit 41 turns on an alarm lamp, flickering the lamp, causes a CRT display 43 to display a message "SUBJECT AGREES TO BE MONITORED" and the speaker 42 to give an aural message "THE SUBJECT AGREES TO BE MONITORED," thereby instructing any physician stationed in the monitor room to examine the subject's facial expression and physical conditions.

Then, in step F, the physician pushes a start switch arranged on the monitor console (FIG. 5), outputting an image-data request signal, which is supplied to the transmission circuit 40. In step G, in response to the image-data request signal, the circuit 40 starts transmitting the image data representing the image of the subject, to the monitor section 2. This step may be omitted.

A video camera installed in the monitor room outputs the image data showing the physician's face, to the robot 5 through the signal transfer path 3. Hence, the display of the robot 5 displays the physician's face. The subject can therefore see the physician on the display. Meanwhile, one of the displays of the monitor console displays the subject's face, which the physician sees. Hence, the subject and the physician can talk, face to face, over the telephone or by means of microphones and speakers.

The physician looks at the subject's face being displayed on the display of the monitor console and also checks the physical conditions being displayed on the other displays of the console, in order to decide what he or she should do for the subject.

The data-acquiring section 1 has various lamps (i.e., light sources). Among these are a ceiling lamp, a bedside reading lamp, and an infrared-ray lamp. If the light coming through the window is insufficient for video-camera monitoring, the physician turns on the ceiling lamp or the reading lamp, or both. After the light-out hour, the physician turns on the infrared-ray lamp, so the video camera 31 built in the head of the robot 5 outputs infrared-ray image data and supplies the data to the monitor section 1 through the signal transfer path 3.

Alternatively, the infrared-ray lamp can be turned on at all times, so that the display of the monitor console can display the infrared-ray image of the subject whenever necessary, at the consent of the subject. No longer is it necessary to adjust the diaphragm opening of the video cameras 31 and 31b in accordance with the brightness of the subject's face, provided that a filter, which allows passage of infrared rays only, is attached to the lens of the video cameras 31 and 31b to filter out the visible light in the daytime. In this case, however, a clearer image of the subject cannot be obtained at the monitor section 2. To obtain a clearer image by means of visible-light image, it is necessary to detach the infrared-ray filter, or to install another video camera exclusively for visible-light image.

For successful visible-light imaging by means of the video cameras 31a and 31b, the diaphragm opening of the cameras 31a and 31b must be adjusted appropriately, in accordance with the brightness of the subject's face. If the sickroom is illuminated mainly by the lamps, scarcely by the natural light coming through the window, whereby the brightness of the subject's face remains substantially the same, the diaphragm opening need not be adjusted at all. If the sickroom is illuminated such that the brightness of the subject's face changes but slightly, the automatic exposure control the video cameras 31a and 31b achieves is sufficient. However, if sunlight merges into the sickroom, greatly varying the brightness of the subject's face and the brightness of any item adjacent to the subject, not only the video camera 31a built in the robot 5, but also the fixed video camera 31b needs complex control, as will be described below.

In the monitor system of FIG. 1, the video camera 31a set in the robot 5 image-senses the face of the subject lying on the bed, whereas the fixed video camera 31b image-senses the whole subject walking in the sickroom and moving on the bed. The video camera 31a built in the robot 5 generates video signals representing the subject's face. The fixed video camera 31b generates video signals showing the whole subject. The video signals output by both video cameras 31 are supplied to the signal processor 32 incorporated in the section 4. The processor 32 can be of any type that can process digital data at high speed.

More specifically, the signal processor 32 has the specific structure shown in FIG. 6. In the processor 32, the video signals generated from the video camera built in the robot 5 or the fixed video camera installed in the sickroom are supplied to an A/D converter 6a, which converts the input video signals into digital signals. The digital signals are supplied to input video-signal bus 6b, and then to n local modules 7-1 to 7-n which are coupled to the video-signal bus 6b.

As is shown in FIG. 7, each of the n local modules 7-1 to 7-n comprises a local processor (i.e., a microprocessor) and a window memory. The window memory stores the video signals representing a given part of the image represented by the video signals being supplied via the input video-signal bus 6b. The local processor processes these video signals. As is evident from FIG. 7, too, a control bus 6c connects the local modules 7-1 to 7-n to the host computer 6d. The host computer 6d controls the other components of the signal processor 32. The local modules 7-1 to 7-n exchange information signals among themselves, and process video signals read out of the window memory 7b, respectively. Each module outputs the processed video signals to a output video-signal bus 6f. A D/A converter 6g converts the video signals on the bus 6f to analog signals. The analog signals, thus obtained, are input to a video monitor 6h. The video monitor 6h displays said given part of the image shown by the video signals supplied through the input video-signal bus 6b.

Each of the local modules 7-1 to 7-n can be of the type shown in FIG. 7. In each local modules of this type, when an address for a desired part of the image is set in the register of a window controller 7a, those video signals representing the desired part of the image and being supplied through the input video-signal bus 6b are loaded into the window memory 7b. A local processor 7c processes the video signals thus stored in the window memory 7b.

The address is set in the register of the window controller 7a from either the host computer 6d or the local processor 7c. The bus interface 7d determines whether the address is supplied from the host computer 6d or the local processor 7c. More specifically, the bus interface 7d connects the control bus 6c to the local bus 7e of the local module, whereby the address supplied from the host computer 6d is written into the register of the window controller 7a. Alternatively, the interface 7d disconnects the control bus 6c from the local bus 7e, whereby the address supplied from the local processor 7c is written into the register of the window controller 7a.

The local modules 7-1 to 7-n can, therefore, operates simultaneously and independently of one another. One of the local modules processes the video signals output by the video camera 31a built in the robot 5, while any one of the other local modules processes the video signals generated by the fixed video camera 31b secured to the wall of the sickroom. Moreover, two or more of the local modules 7-1 to 7-n can process the video signals generated by one and the same video camera, thus each performing a different operation on these video signals; the operations can be completed within a shorter time than in the case where one local module carries out the different operations, one after another. If necessary, two or more local modules can perform parts of an operation on the video signals output by either video camera 31a or 31b, thereby to complete the operation within an even shorter period of time.

The robot 5 is located at the position where the video camera 31a built in it can best cover the subject who usually lies on the bed. A cable connects the robot 5 to a local station installed in the sickroom. The local station transfers various signals between the robot 5, on the one hand, and the monitor section 2 and the data-processing/control section 4, on the other hand. Further, the local station supplies electric power to the robot 5, thereby charging the battery incorporated in the robot 5.

Figure 8A:
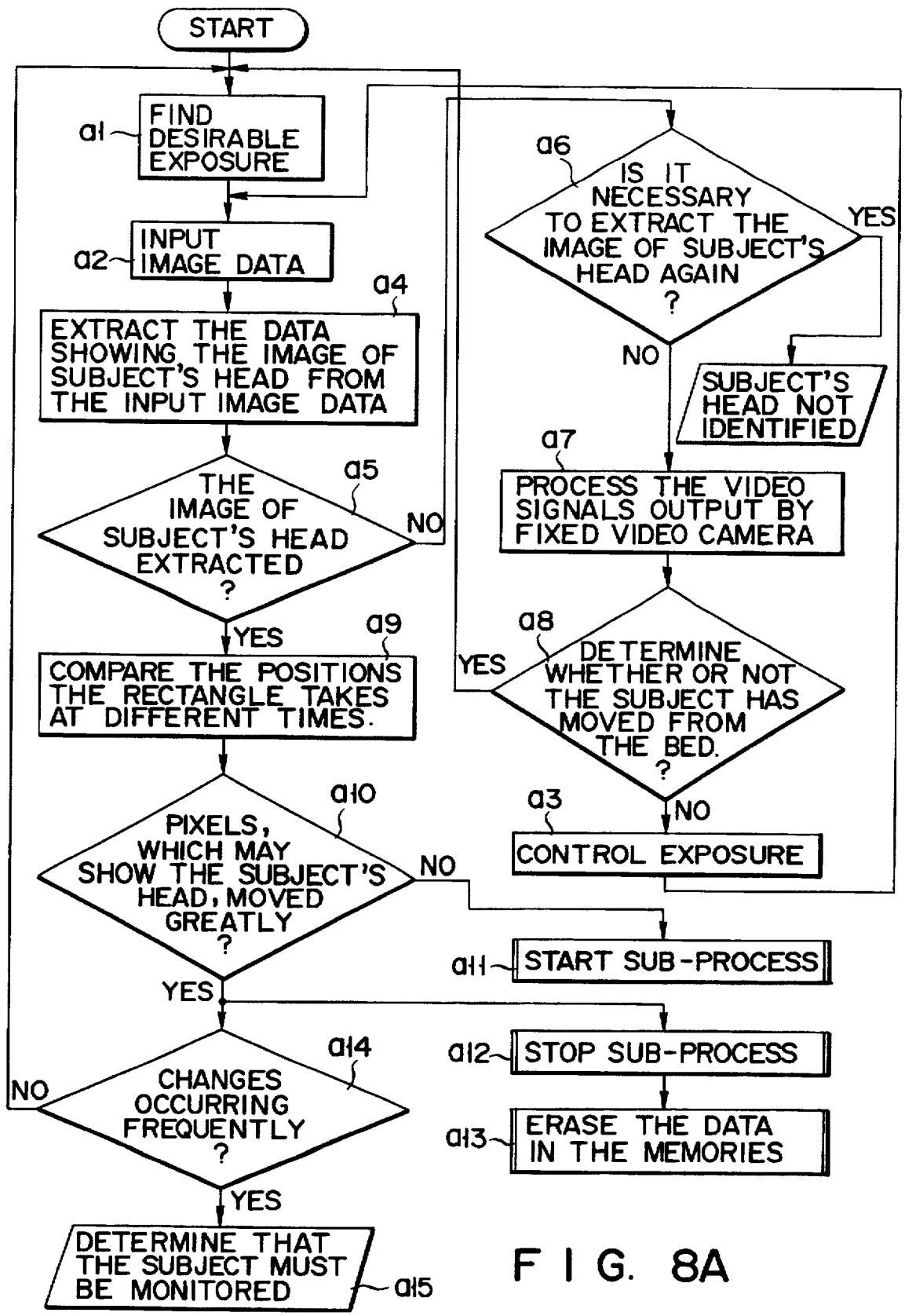
FIGS. 8A and 8B are a flow chart explaining how the image-processing apparatus processes the image of a subject which the camera built in the robot has taken.
Figure 8B:
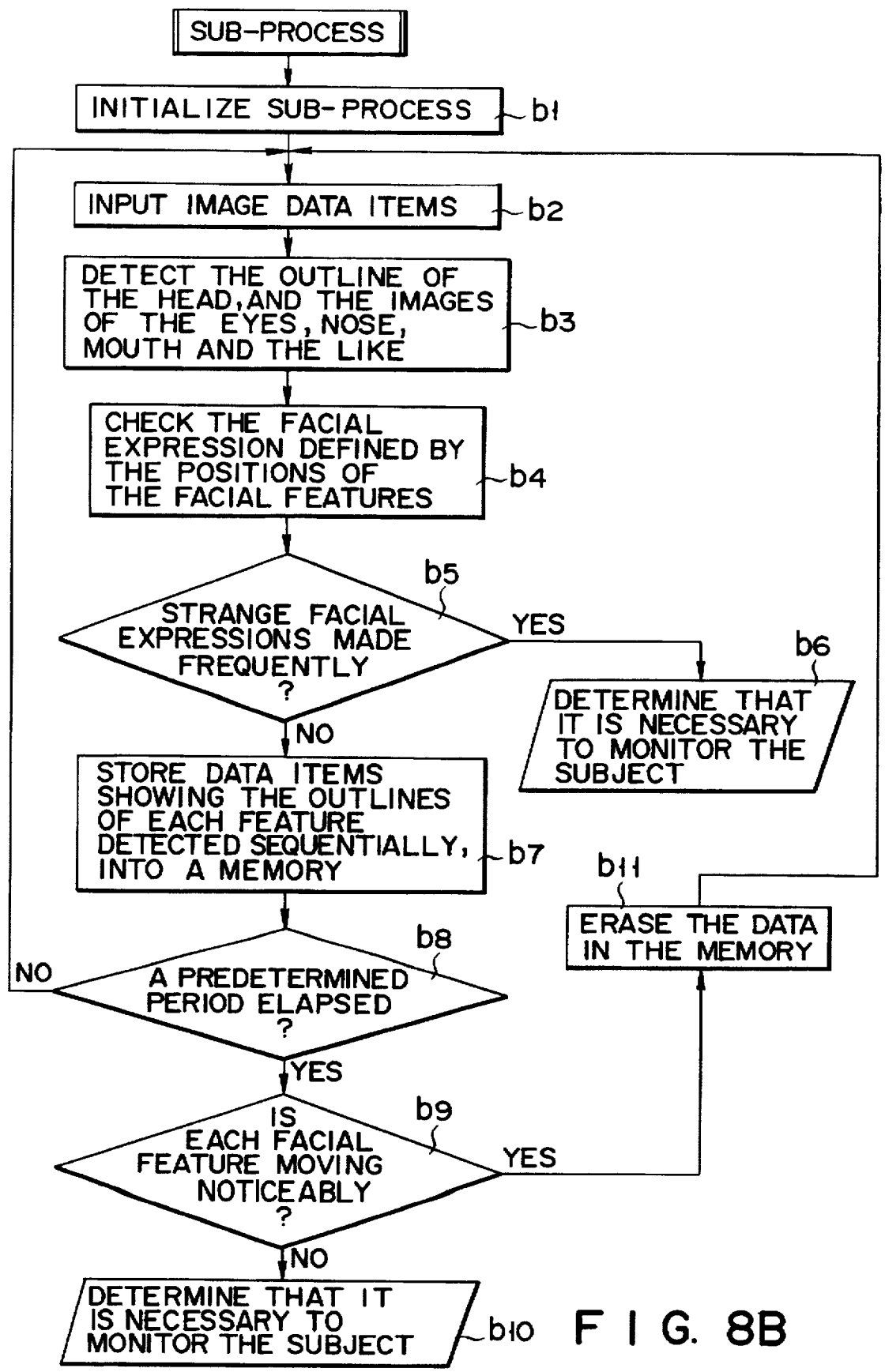

It will now be described how the signal processor 32 incorporated in the data-processing/control section 4 processes the video signals output by the video camera 31 built in the head of the robot 5, with reference to the flow chart of FIGS. 8A and 8B.

Since the video camera 31a built in the robot 5 is directed to only the subject on the bed, the brightness of the image the camera 31a image-senses does not change greatly. Hence, an desirable exposure is determined, in step a1, by means of the ordinary automatic exposure device built in the video camera. Then, in step a2, both video cameras 31a and 31b start image-sensing the subject and generating video signals showing the subject. If the quality of the video signals, thus generated, do not meet the required standards, the operation goes to step a3. In step a3, the exposure is controlled by changing the diaphragm opening and shutter speed of the video camera 31a incorporated in the robot 5.

The video signals output by the video camera 31a are subjected to a main process and a sub-process in the signal processor 32. The main process is continuously performed at all times, as is evident from FIG. 8A. The sub-process is set up from the main process and carried out, only when necessary, as is evident from FIG. 8B.

In the main process, the signal processor 32 samples the image data at regular intervals, thereby extracting image-data items representing the head of the subject. From the image of the head, the abnormality decision circuit 34 determines whether or not the subject is in critical conditions. More specifically, if the head moves greatly as when the subject turn over in the bed, the circuit 34 determines that the subject is not in critical conditions. If the head moves rather frequently, the circuit 34 determines that there may be something wrong with the subject.

The sub-process is performed when it is determined, from the results of the main process, that the subject does not move his or her head much. In the sub-process, the signal processor 32 samples the image data at shorter intervals, thereby extracting image-data items representing the eyes, nose and mouth of the subject. The facial expression defined by the position relation among the images of the eyes, nose and mouth is compared with the reference expressions which the subject shows in his or her normal conditions. If the facial expression is different from any one of the reference expressions, the abnormality decision circuit 34 determines that it is necessary for the physician to examine the physical conditions of the subject. Also in the sub-process, the signal processor 32 integrates the data items showing the outlines of the head, face, eyes, nose and mouth, for a predetermined period of time, thereby determining whether or not these outlines move as the subject breathes. If YES, it is determined that the physician need not to examine the subject. If NO, it is determined that something is wrong with the subject, and that the physician must examine the subject.

Figure 10:
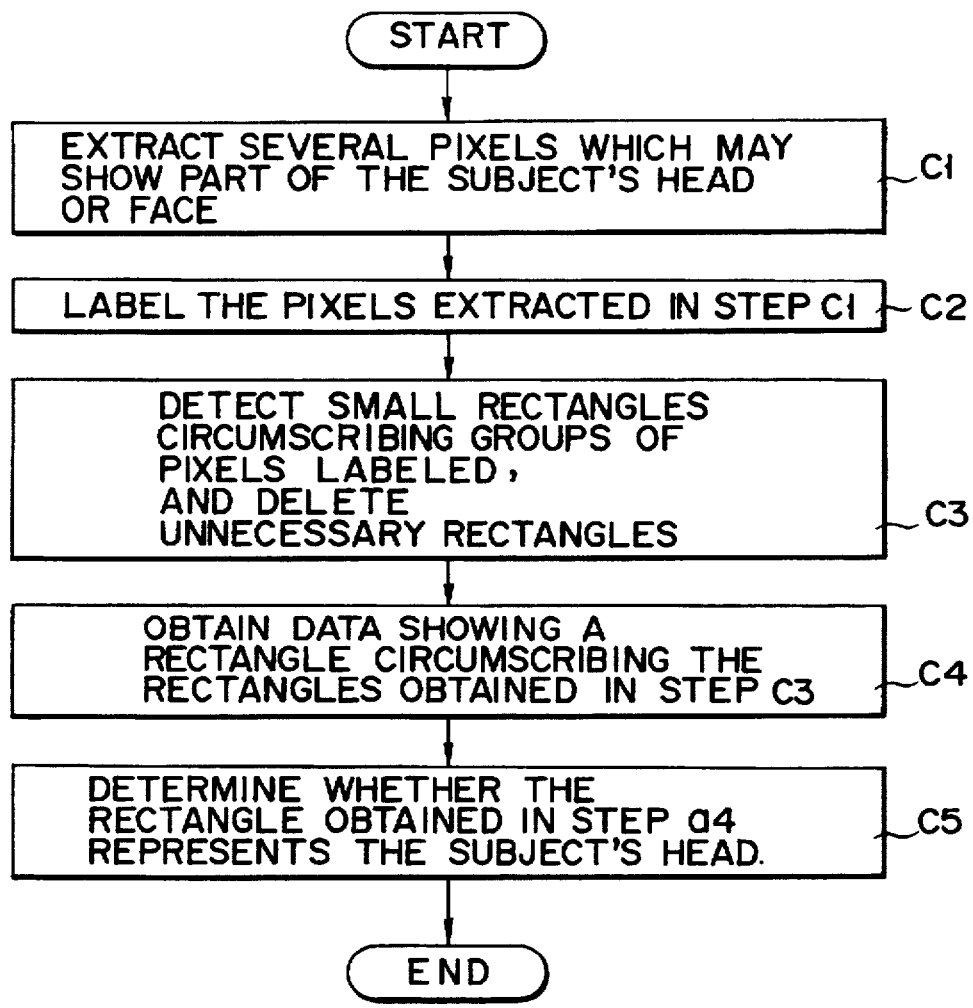
FIG. 10 is a flow chart illustrating how the image-processing apparatus extract the data items representing the subject's head.

As been described, in the main process, the signal processor 32 samples the image data, thereby extracting image data representing the head of the subject, in step a4. The image-data sampling will be explained in more detail, with reference to the flow chart of FIG. 10.

First, in step c1, pixels which may represent part of the subject's head are extracted. In other words, the pixels are distinguished from those representing the pillow, bed sheet and blanket. If the video camera 31a incorporated in the robot 5 is a color camera, the pixels of skin color and hair color are extracted from the pixels of other colors. If the camera 31a is a monochrome one, the pixels showing part of the subject's head are distinguished from those representing the bedding, in accordance with the brightness or texture of pixels.

The data showing the constant features of the beddings is previously registered, so that the pixels showing the bedding can easily be distinguished from those representing the subject's head. Alternatively, the pixels showing the bedding can be distinguished from those showing the subject's head, by identifying them with the greater part of a feature histogram, since the image of the beddings occupies more than half of the image formed by the video camera 31 incorporated in the robot 5. The either method can successfully extract the pixels which may represent the subject's head, from the pixels which represent the pillow, bed sheet and blanket.

In addition to these methods, there are some other methods of extracting the pixels which may show the subject's head, from those representing the bedding. One of the methods is used, or some of them are employed in combination, in order to extract the pixels from those showing the bedding with the highest accuracy possible.

The methods for identifying the subject are selected in accordance with the known feature of the bedding or the feature of the bedding which is obtained by an image processing. This selection is realized by deciding the relation between the feature of the bedding and the identification method and inserting the relation in a selection algorithm.

Another of the methods is to process vectors, each showing the features of a pixel. More specifically, the feature vectors are classified by the method commonly used in pattern recognition, thereby distinguishing the pixels showing the subject's head from those representing the beddings.

Still another method is to convert the features of pixels to digital values and then to compare the sum of the digital values of any adjacent pixels with a reference value, thereby distinguishing the pixels representing the subject's head from the pixels showing the pillow, bed sheet and blanket.

Another method is to prepare a histogram of the pixel features, and distinguish that portion of the histogram which is clearly different from the remaining portion and which seems to represent the subject's head.

Another method is to distinguish the individual pixels, which seem to represent the tiny portions of the subject's head, from the other pixels forming the input image, and then to combine the pixels of each group, thus distinguished, thus forming a rectangle. The several rectangles, thus formed, are combined into a larger rectangle, which may represent the subject's head.

All the methods described above can be applied to perform steps c1 to c5 (later explained). If the results obtained are different, from method to method, the methods are carried out again, or the the results of one method which are considered more reliable than those of any other method carried are used to extract the image of the subject's head from the input image.

Instead, one of the methods described above can be carried out, which best fits the conditions under which to extract the image of the subject's head from the input image.

In the present embodiment of the invention, a plurality of local modules can be used to process the video signals representing the pixels forming the input image, whereby the input image can be processed at higher speed than otherwise.

Figure 11A:
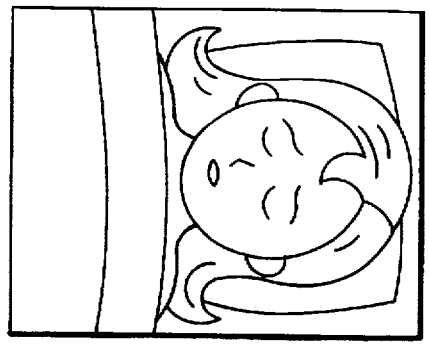
FIGS. 11A to 11D are diagrams explaining the process of extracting the data items showing the subject's head.
Figure 11B:
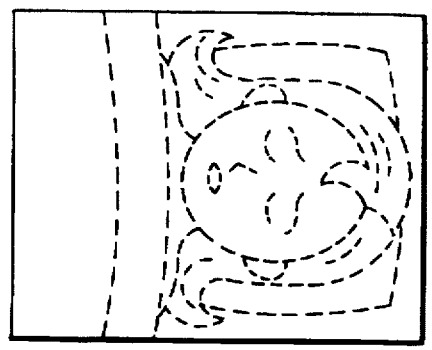

The pixels extracted from the input image shown in FIG. 11A and defining the image shown in FIG. 11B are labeled in step c2. Then, in step c3, the video signals representing the labeled pixels are processed, whereby data items are obtained which define rectangles. Each of these rectangles circumscribes a groups of the labeled pixels which are close to one another. Of these rectangles, those which are so small to be regarded as resulting from noise, and those which are long enough to be regarded as representing a crease of the bedding are deleted from the image, thereby forming the image shown in FIG. 11C.

Figure 11C:
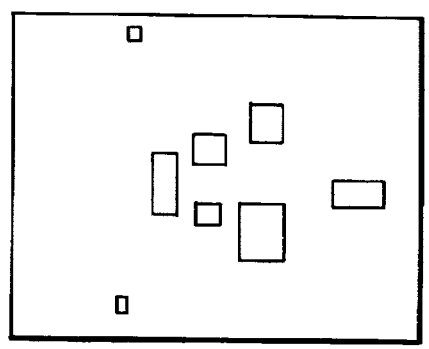
Figure 11D:
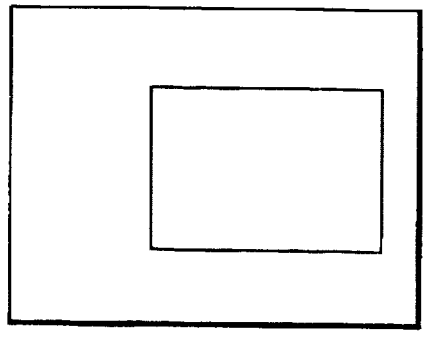

Then, in step c4, data is obtained which represents a rectangle circumscribing the rectangles shown in FIG. 11C, as is illustrated in FIG. 11D. In step c5, it is determined whether or not the rectangle is large enough to represent the subject's head. If YES, the rectangle is considered to represent the subject's head. If NO, the rectangular area is expanded so that it can be understood to represent the subject's head. Thus, the image of the subject's head is extracted from the input image (FIG. 11A), and a flag is set at value "1," indicating that the subject is in the bed.

In step a5, it is determined whether or not the image of subject's head has been extracted from the input image (FIG. 11A) in step c5, in accordance with the value of the flag. If NO, the operation goes to step a6, in which it is determined whether or not the image of the subject's head must be extracted again from the input image. If YES, steps a4 and a5 are performed. If NO, the operation goes to step a7. In step a7, the signal processor 32 processes the video signals output by the fixed video camera 31b. In step a8, it is determined, from the processed video signals, whether or not the subject has moved from the bed. If YES, that is, if the subject has moved from the bed, it is unnecessary to extract the image of the subject's head from the image input from the video camera 31 incorporated in the robot 5. In this case, the operation returns to step a1.

If NO in step a8, that is, if the subject is in the bed, but the image of the subject's head has not been extracted from the image input from the video camera 31b built in the robot 5, the operation goes to the next step a3. In step a3, the diaphragm opening and shutter speed of the video camera 31a built in the robot 5 are adjusted, thereby controlling exposure. The exposure control is required when the sunlight illuminates the bed, and the image input by the video camera 31a thereby has bright portions and dark (i.e., shaded) portions.

Figure 12:
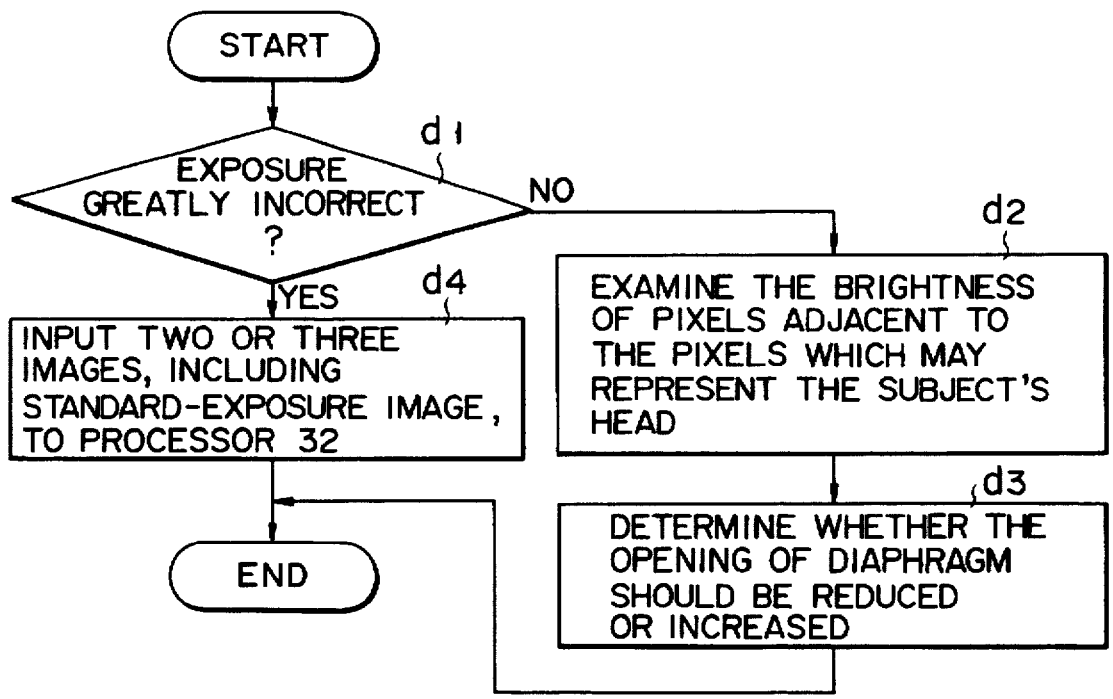
FIG. 12 is a flow chart explaining the process of examining the inputting and processing of image data.

With reference to the flow chart of FIG. 12, it will be explained how to control the exposure in step a3.

First, in step d1, it is determined whether or not the exposure is greatly incorrect. More precisely, pixels brighter or darker than desired are counted. If the input image has more excessively bright pixels than a predetermined number, the exposure is regarded as very excessive. If the input image has more excessively dark pixels than the predetermined number, the exposure is regarded as very insufficient. If NO in step d1, this means that the exposure is either correct or slightly incorrect, and that the pixels which may represent the subject's head have desired brightness or are a little too bright or a little too dark. In this case, it can be said that quite a few pixels showing the subject head have been detected, though the image of the subject's head could not be extracted from the input image in step a5. The operation goes to step d2. In step d2, the pixels adjacent to the pixels which seem to represent the subject's head are examined for their brightness. Then, in step d3, it is determined, based on the brightness of the adjacent pixels, whether the opening of the diaphragm of the video camera 31a must be reduced or increased. More specifically, the diaphragm opening must be decreased if the adjacent pixels are too bright, and must be increased if the adjacent pixels are too dark. A control signal is supplied to the diaphragm drive device incorporated in the video camera 31a, whereby the opening of the diaphragm is reduced or increased to control the exposure correctly.

Figure 13:
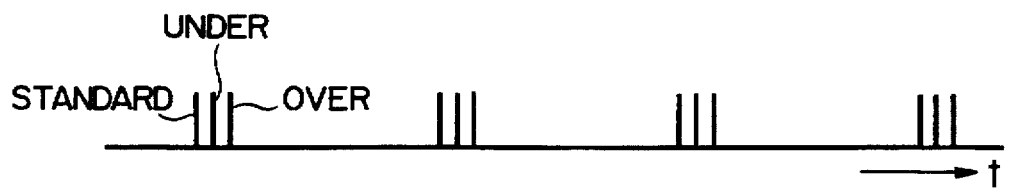
FIG. 13 is a diagram illustrating the timings of inputting image data, which differ in accordance with various exposure conditions.

On the other hand, if YES in step d1, that is, if the exposure is greatly incorrect, this means that many of the pixels forming the input image are either too bright or too dark. In this case, the operation goes to step d4. In step d4, the video camera 31a built in the robot 5 is driven repeatedly under three different exposure conditions, as is shown in FIG. 13, thus generating video signals representing three images of the subject, i.e., an over-exposure one, a standard-exposure one, and an under-exposure one. If the input image has over-exposure portions only, the video signals representing the standard-exposure and under-exposure images are input to the signal processor 32. If the input image has under-exposure portions only, the video signals showing the over-exposure and standard-exposure images are input to the processor 32. If the input image has both under-exposure portions and over-exposure portions, the video signals showing the over-exposure, standard-exposure and under-exposure images are input to the signal processor 32.

Figure 14:
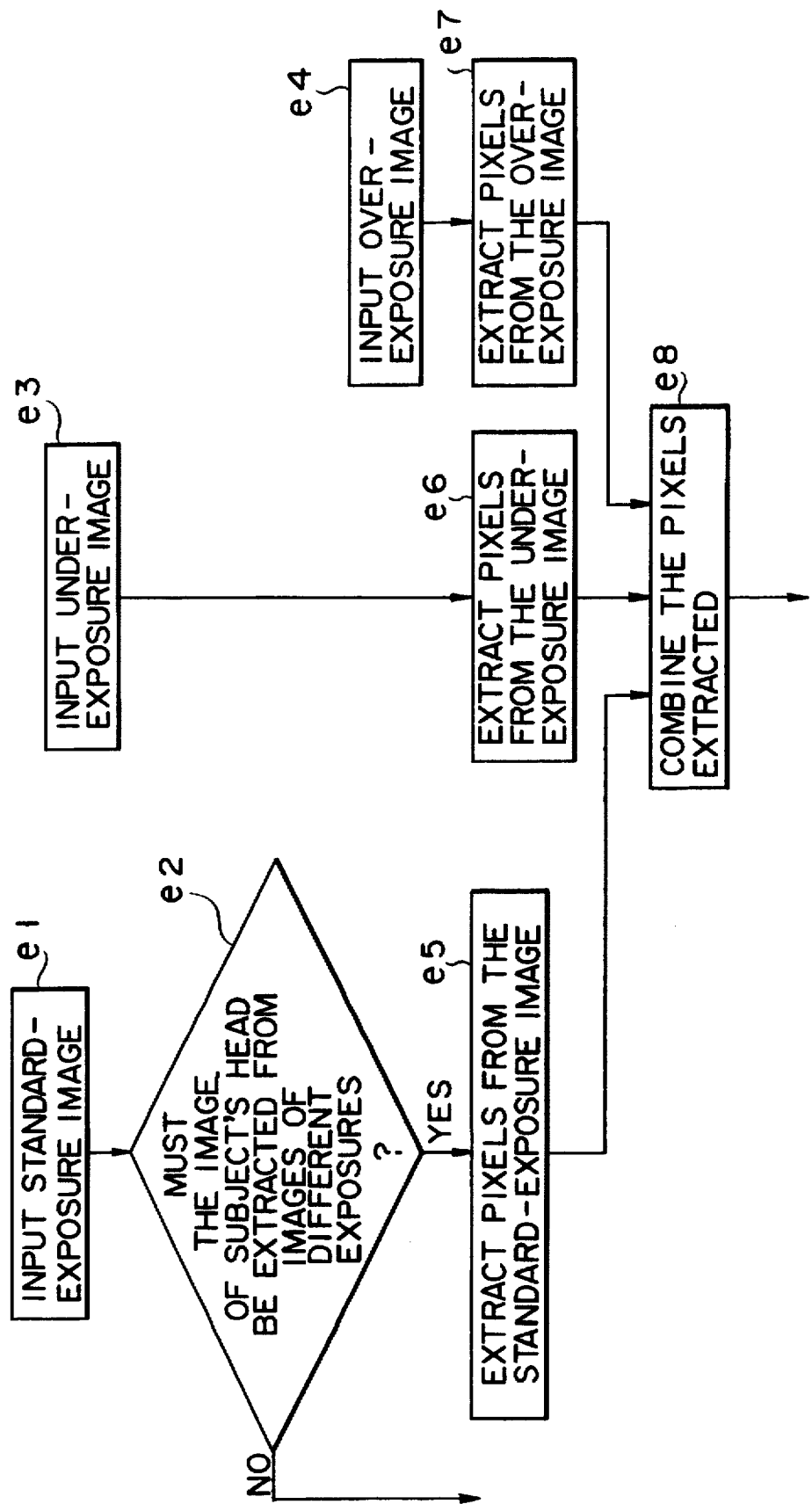
FIG. 14 is a flow chart explaining how the image-processing apparatus performs its function in accordance with the exposure condition selected.

In the processor 32, designated three of the local modules 7-1 to 7-n process the over-exposure image, the standard-exposure image and the under-exposure image, respectively, which have been formed by the video camera 31a, thereby to extract, in step a4, the image of the subject's head from the image (FIG. 11A) input from the video camera 31a incorporated in the robot 5. With reference to the flow chart of FIG. 14, it will be explained how the processor 32 performs step a4.

In step e1, the standard-exposure image input to the signal processor 32. In step e2, the first designated local module processes the video signals representing the standard-exposure image, thereby detecting those portions of this image which are too bright and too dark. From the brightness and darkness of these portions, it is determined whether or not the image of the subject's head must be extracted from the input image by using images of different exposures. More specifically, if the number of the excessively bright and dark portions detected is less than a predetermined value, that is, if the exposure is substantially correct, it is determined that the image of the subject's head must be extracted from the standard-exposure image only. If the number of the excessively bright and dark portions detected is greater than the predetermined value, it is determined that the signals showing the bright portions must be processed by using an under-exposure image, the signals showing the dark portions must be processed by using an over-exposure image, and the signals showing the other portions of the image must be processed by using the standard-exposure image.

In the meantime, the under-exposure image is input to the processor 32 in step e3, and the over-exposure image is input to the processor 32 in step e4.

If it is determined, in step e2, that the image of the subject's head must be extracted by using the under-exposure, over-exposure and standard-exposure images, the designated three of the local modules of the signal processor 32 perform the following operations. In step e5, the first designated local module extracts the pixels showing the subject's head from the standard-exposure image. In step e6, the second designated local modules extracts the pixels representing the subject's head from the under-exposure image. In step e7, the third designated local module extracts the pixels representing the subject's head from the over-exposure image. Then, in step e8, the pixels which may represent the subject's head and which have been extracted from the standard-exposure, under-exposure and over-exposure images are combined, thus extracting the pixels showing the subject's head in the same way as such pixels are extracted from the input image shown in FIG. 11A.

Thereafter, the operation goes to step a5, just as in the case where the image of the subject's head is extracted from one image only. In step a5, it is determined whether or not the image of subject's head has been extracted from the input image shown in FIG. 11A.

Since the standard-exposure image, the under-exposure image, and the over-exposure image are not ones which have been obtained at the same time, the rectangular area (FIG. 11D) representing the subject's head expands. In the case where the subject moves fast, and the operation moves to step a10, skipping step a9. In step a10, it is determined whether the pixels which may represents the subject's head have moved greatly or not.

If NO in step a5, that is, if the image of the subject's head cannot be extracted despite the second trial, it is determined in step a6 that the image of the subject's head can no longer be extracted from the image input from the video camera 31a built in the robot 5 or from the image input from the fixed video camera 31b. This is the case where the subject is out of the view field of both video cameras 31a and 31b.

If YES in step a5, the operation moves to step a9. In step a9, the position of the rectangle (FIG. 11D) in the image input from the video camera 31a is compare with the position of the rectangle in the image input some time ago. In step a10, it is determined whether or not the rectangle has moved by a distance longer than a predetermined value. If NO, the operation goes to step a11, in which the sub-process is set up, which will later be described. If YES in step a10, the operation goes to step a12 and also to step a14. In step a12, the sub-process is stopped if the sub-process has been performed. Then, in step a13, the data in a memory (later described) used in the sub-process in order to detect minute movements of the subject is erased.

Meanwhile, in step a14, it is determined whether or not the rectangle (FIG. 11D) moves greatly at a frequency higher than a predetermined value. If YES, it is determined in step a15 that the subject must be monitored and examined in the monitor room. If NO in step a14, the operation returns to step a1.

The sub-process, mentioned above, will be explained, with reference to the flow chart of FIG. 8B.

If NO in step a10, that is, if the rectangle has not moved by a distance longer than a predetermined value, the sub-process is initialized in step b1. More specifically, the local modules of the processor 32 process video signals, detecting the angle by which the subject faces away from the video camera 31a, and the positions of the subject's eyebrows, eyes, ears, nose and mouth. Step b1, i.e., the initialization of the sub-process, will be described with reference to the flow chart of FIG. 15.

Figure 15:
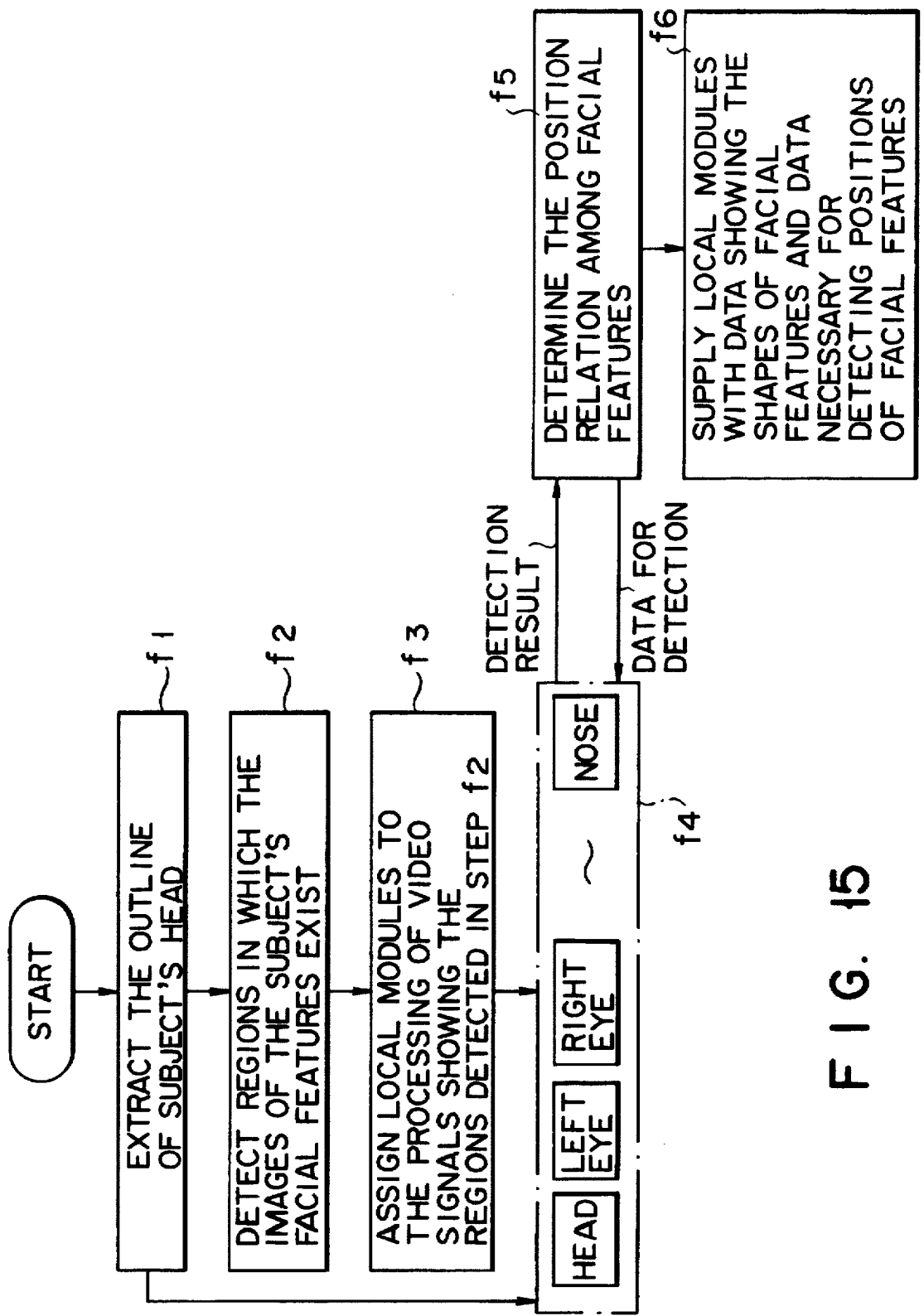
FIG. 15 is a flow chart explaining the initial stage of the sub-process which the image-processing apparatus performs on the image data supplied from the camera incorporated in the robot.

As can be understood from FIG. 15, in step f1, one of the the local modules processes the video signals representing those pixels near the sides of the rectangle (FIG. 11D), thereby detecting the outline of the subject's head. Then, in step f2, the regions within the rectangle, in which the images of the subject's eyes, nose, and month possibly exist, are detected. At this stage, the regions detected are not so small since which way the subject faces away from the video camera 31a has not been determined yet. Next, in step f3, other local modules of the processor 32 are assigned to process the video signals representing the regions detected in step f2.

In step f4, the local modules process the video signals, thereby detecting the images of the user's eyes, nose and mouth. More precisely, the local modules detects the pixels forming the outlines of the eyes, nose and mouth. They output the data items representing the positions of the outlines of the eyes, nose and mouth. These data items are supplied to designated one of the remaining local modules or to the host computer 6d (FIG. 6).

In step f5, the designated local module or the host computer 6d determines the position relation among the user's eyes, nose and mouth, from the data items supplied from the local modules, and also determines the angle by which the subject faces away from the video camera 31a from the position relation among the subject's facial features. In step f6, the designated local module or the host computer 6d supplies the local modules with the data items representing the shapes of the subject's facial features, and also the data required for determining the positions of the facial features.

As can be understood from FIG. 16, the facial features of the subject, e.g., the eyebrows, the eyes, the nose, the ears, the mouth, have the position relation which is common to human beings. This relation is defined by the positions of individual facial features with respect to the vertical and horizontal directions, and also by the distances between the facial features. The designated local module or the host computer 6d can, therefore, determine the positions of the facial features detected in step f4, in accordance with the data representing said position relation. To detects the images of the facial features, the vertical center line of the subject's face is first detected from the outline of the subject's head, the angle by which the subject faces away from the video camera 31a is then determined from the position of the center line and the position of the top of the head. More specifically, the host computer 6d determines the angle from the positions of the vertical center line of the face and the top of the head, and then determines the position relation among the facial features. If any facial feature detected is not located at the position it should take, it will be identified in accordance with its position with respect to those of the other facial features detected later. If the facial feature cannot be identified, the local module assigned to the region in which the facial feature may exists processes the video signals representing the region, for the second time.

The image of the subject's face, shown in FIG. 16, is what the video camera 31a built in the robot 5 forms when the subject faces straight toward the camera 31. Needless to say, the position relation among the subject's facial features changes from the one shown in FIG. 16, when the subject faces away from the video camera 31a. When the subject greatly faces away from the video camera 31a, some facial features may disappear from the image the video camera 31a forms, and the shapes of the some other facial features will change.

The changes in the positions and shapes of some facial features are limited, however, by the positions where they are detected within the outline of the subject's head and the angle by which the subject has faced away from the video camera 31a. Let us compare the subject's head to a cylinder as is shown in FIG. 17A. In this case, if the image of the mouth is located slightly left to the vertical center line as is shown in FIG. 17B, then it is determined that the subject has faced a little to the right, away from the video camera 31 built in the robot 5. The same holds true of any facial feature other than the mouth.

The data showing the relation between the positions of the facial features detected, on the one hand, and the angles by which the subject faces away from the camera 31a, on the other, is registered, as a set of rules, in the host computer 6d. The host computer 6d examines the images of the facial features are examined against these rules, thereby calculating the angle by which the subject has faced away from the video camera 31a.

As has been pointed out, a facial feature may disappear from the input image in some cases. In such a case, it is determined that the subject has greatly faced away from the camera 31a in one direction or an other. For instance, when both eyes and the greater part of the nose disappear from the image, it is ascertained that the subject has faced upward. When only the ears are seen in the image, it is determined that the subject has faced further upward.

The position and shape of one facial feature, or those of a few facial features can help to deduce the angle and direction in which the subject has faced away from the camera 31a. Once the angle and the direction are thus deduced, it is possible to determine the positions of the other facial features which are not seen in the input image. The shape of the nose changes quite noticeably as the subject faces to the left or the right, away from the video camera 31a. Hence, the shape of the nose as seen in the input image helps to determine the angle and direction in which the subject has faced away from the camera 31a. The data showing the angle and the direction is supplied to the local modules incorporated in the signal processor 32, so that the modules may detect the positions of the facial features with higher accuracy than otherwise.

When an image of an eye is seen in the input image, it is difficult to ascertain which eye it is, the left eye or the right eye, up until the other eye or any other facial feature is detected so as to determine which way and how much the subject has faced away from the camera 31. The local module assigned to the left-eye region, for example, is assigned anew to the right-eye region, if the eye seen in the input image has turned out to be the right eye. In this case, the local module assigned to the right-eye region is assigned anew to the left-eye region.

Some facial features are easy to detect, and other features are hard to detect, because of the difference in size. Since the mouth, i.e., the largest facial feature, is very easy to detect, the mouth is detected first. Then, the ears, i.e., the next largest facial features, are detected next, more easily than the mouth since the ears have a specific relation to the mouth in terms of position. Next, the nose, the eyes, and the eyebrows are detected, in this order, more easily than the features already detected.

After step b1, i.e., the initialization of the sub-process, is executed, the sub-process goes to step b2. In step b2, the signal processor 32 samples the image data at shorter intervals as is shown in FIG. 9B, thereby extracting image-data items representing the eyes, nose and mouth of the subject. In step b3, the local modules 7-1 to 7-n of the processor 32 processes the video signals representing these facial features, thus detecting the images of the facial features.

Next, in step b4, the position relation of the facial features is checked against the standard position relation the features have when the subject is at rest, either awake or asleep. If the position relation is much different from the standard relation, it is determined that the subject is in abnormal condition. At the same time, the changes, if any, in the shapes of the facial features can be checked. (For example, it is checked whether the lips are rounded, whether the mouth is opened up, and so forth.)

In step b5, it is determined whether or not the subject makes strange facial expressions (each defined by the positions of the facial features) frequently. If YES, the operation goes to step b6, in which it is determined that the subject is in abnormal condition, and should, therefore, be monitored and examined by a physician. If NO, the operation goes to step b7. In step b7, the data items obtained at different times, each representing the outline of each facial feature, are stored into a memory (not shown). More precisely, a plurality of memories is used. Each memory accumulates the data items obtained successively and representing the outlines of a facial feature. For example, the memory assigned to store the data about the mouth accumulates the data items representing the various outlines t1, t2, t3, . . . of the subject's mouth which are shown in FIG. 18.

Thereafter, in step b8, it is determined whether a predetermined period has elapsed or not from the time the memories started accumulating the outline-data items. If NO, the operation returns to step b2, whereby steps b2 to b7 are repeated. If YES, in step b8, the operation moves to step b9. In step b9, it is determined whether or not the number of pixels accumulated in each memory is greater than the number of pixels defining the outline of the feature detected at a given time. If NO, that is the facial feature does not move at all, the operation goes to step b10. In step b10, it is determined that the subject is in abnormal condition and should, therefore, be monitored and examined by a physician. If YES, that is, the facial feature is moving slightly due to, for instance, breathing, the operation moves to step b11. In step b11, all memories are reset, erasing the data stored in them.

As has been explained with reference to FIG. 8A, in step a7, the signal processor 32 processes the video signals output by the fixed video camera 31b, thereby to detect the subject's head, but also determine where in the sickroom the subject is now. How the processor 32 performs this step will be explained in detail, with reference to the flow chart of FIGS. 19A and 19B.

The fixed video camera 31b scans a greater area than the video camera 31a in the robot 5 located neat the bed. In addition, some part of the sickroom is illuminated with the sunlight, while other parts are not, and the brightness of each part of the sickroom changes as the day's hours pass, one by one. Hence, the brightness of the view field of the fixed camera 31b changes more than that of the view field of the video camera 31a on the robot 5. Thus, much care must be taken to set conditions under which to input image data to the signal processor 32, including the exposure condition suitable for the fixed video camera 31b.

First, the best possible exposure conditions for the fixed video camera 31b are determined in step g1, by means of the ordinary automatic exposure device built in the fixed video camera 31b. If it is expected that the brightness of the view field changes greatly, a standard-exposure image, an under-exposure image, and an over-exposure image input. The local modules of the processor 32 process the video signals representing these images of different exposures, and combine the pixels of these images—in the same way as in the processing of the video signals output by the video camera 31a in the robot 5.

The image of any still object in the sickroom, such as a piece of furniture, appears at the same position in the image input from the fixed video camera 31b, unless the subject stands in front of the object, hiding the object behind his or her back. The brightness of at least one designated portion, which is shaded in FIG. 20, of each piece of furniture is detected, and the exposure is determined from the brightnesses of the designated portions of the various items of furniture. This is done in the specific method, which will be explained with the reference to the flow chart of FIG. 21.

First, the standard-exposure image formed by the fixed video camera 31b is input to the signal processor 32 in step h1. Then, the designated portions of the still objects, seen in the input image, are counted in step h2. In step h3, it is determined whether or not the number of the designated portions detected in step h2 is greater than a predetermined value, or whether or not they have been correctly detected. If NO, the operation goes to step h4, in which the exposure condition of the fixed video camera 31b is altered, and the image the camera 31 takes in the altered exposure condition is input to the signal processor 32. In this case, the operation returns to step h2. Steps h2, h3 and h4 are repeated until an affirmative decision is made in step h3. If YES in step h3, that is, if the number of the designated portions detected in step h1 is greater than the predetermined value, the operation moves to step h5. In step h5, it is determined which one of the images showing the identical designated portion of each still object, which most correctly represents the designated portion and which should therefore processed in the sub-process.

Step h2 will be described in greater detail. The local modules incorporated in the signal processor 32 are assigned to the detection of the designated portions of the still objects, respectively. When any local module detects the designated portion of the still object, it means that the module detects no other portion of the still object which need not be detected at all. The local module applies an outline-detecting operator to the video signals representing the designated portion detected, and digitizes these video signals, thereby detecting the outline of the designated portion of the still object. Further, the length of the outline thus detected is divided by the actual length of the designated portion. If the ratio of the detected length of the outline to the actual length of the designated portion is greater than a threshold value, the portion is regarded as having been correctly detected. The length ratio for each designated portion correctly detected is stored in a memory, and will be used to check the entire image of the sickroom.

The best possible exposure condition varies, from one designated portion to another designated portion. Unless the difference between the best exposure conditions for any two adjacent designated portions is relatively great, the same exposure can be applied to the adjacent designated portions. Hence, if the outline of a given designated portion is not correctly detected, it can be detected in the image which the fixed video camera 31b forms in the exposure condition best for the designated portions which are adjacent to the given designated portion.

As has been explained with reference to FIG. 21, images of various exposures are input, one after another, to the signal processor 32, and the designated portions of each input image are detected. Instead, several images of different exposures can be input simultaneously input to the processor 32, and then the designated portions of each image are detected.

In the instance described above, the exposure condition best for each designated portion of a still object is determined by the ratio of the length of the outline of the portion to the actual length of the portion. Alternatively, the best possible exposure condition can be selected for each designated portion in accordance with the brightness of the designated portion. Further, if the fixed video camera 31b is a color video camera, the exposure condition can be determined by the hue (i.e., RGB-density ratio) of the designated portion.

The object of performing step gi (FIG. 19A) is to detect whether or not the subject is moving in the sickroom. Thus, the fixed video camera 31b inputs images of the sickroom to the signal processor 32 at intervals of several seconds to tens of seconds. The exposure condition can be changed, either at these intervals or at longer intervals.

After the most appropriate exposure condition has been determined, the image is input from the fixed video camera 31b to the signal processor 32. In the processor 32, some of the local modules 7-1 to 7-n processes the video signals representing the designated portions of the still objects. Then, in step means g2, changes, if any, are detected in the images of the designated portions. There are various types of changes that may occur in the image of each designated portion. Also, various methods are available for detecting these changes. The best possible method is selected in accordance with the lighting condition in the sickroom and the exposure condition of the fixed video camera 31b. The results of only one method may fail to show whether changes are occurring. In this case, two or more methods can be employed in combination.

Three major methods available for detecting changes that may occur in the image of each designated portion are as follows:

[Finding Difference between Two Consecutive Images]

This method is to detect a region of the image, which has undergone a great change between two times the fixed video camera 31b takes two pictures of the sickroom, respectively. The method is effective in the case where the moving object, i.e., the subject, has a sharp contrast with respect to the background. In order to obtain a great difference between two images, the data items representing these images can be subjected to smoothing process or differentiation.

[Comparison of Pixel Hues]

The method is employed when the fixed video camera 31b is a color video camera. In this method, the RGB-density ratios of the individual pixels forming the last image input to the processor 32 are compared with those of the pixels forming the penultimate image input to the processor 32. Of the pixels, those whose RGB-density ratios have varied greatly are considered to define regions which have undergone a prominent hue change. This method of detecting changes occurring in the input image is effective in the case where the moving object, i.e., the subject, is of a color different from that of the background, even if the two consecutive images input to the processor 32 have been formed in different exposure conditions.

[Comparison of Edges]

This method includes steps of dividing the image into a plurality of small square regions, comparing the edge included in each of the present divided regions with that in each of the previous divided regions, and processing, when the edge is varied between the previous and present regions, the corresponding region as the varied region. This method is more effective in relation to the variation of the image input condition, etc., in comparison with the aforementioned process for obtaining the difference between the present and previous regions. However, if the background and the moving object have a texture containing many edges, it is impossible to detect the movement of the moving object only by checking the edges in the small region. Accordingly, for the purpose of avoiding the above disadvantage the image is divided so that the divided region has a size larger than that of the element constituting the texture. On the basis of this condition, the actual element of the texture is obtained, and it is decided whether or not a difference exists between the texture elements.

Whether the changes, if any, in the input image can be successfully detected or not largely depends on the properties of the moving objects and those of the background objects. The moving objects are the subject's head and the clothes he or she wears, and the background objects are the walls, the floor, and the bedclothes. Of the moving and background objects, those which may change in shape are the clothes and the bedclothes.

The data representing the properties (brightness, color, texture, and the like) of the other objects is input into the host computer 6d, either by a human operator or through data-processing. To be more specific, the brightnesses of the pixels forming the input image are classified into a proper number of scales, and the colors of these pixels are classified into various types in accordance with the RGB-density ratios of the pixels. Then, those of the pixels forming the input image, which are relatively dark and of relatively dark colors, are regarded as defining the creases of the clothes and bedclothes.

Whenever the bedclothes are replaced with new ones, the operator may input the data representing the properties of the new bedclothes, such as texture, color, patterns, etc., into the host computer 6d. Alternatively, the properties of the bedclothes can be determined by extracting the pixels forming the image of the bedclothes, from the input image, which can easily be accomplished since the position of the image of the bedclothes is known and not changeable. The properties of the bedclothes can be thus determined, either at the time the bedclothes are changed to new ones, or at predetermined intervals.

The operator can store into the host computer 6d the data representing the properties of the subject's head, including those of his or her facial features.

Similarly, the operator can stores into the host computer 6d the data showing the properties of the clothes the subject wears, whenever the subject change dresses. Alternatively, the data representing the properties of every garment which the subject may wear can be registered in the host computer 6d beforehand, and can be read therefrom when the subject changes dresses to that garment. The data representing the image of the clothes the subject wears can be automatically input to the host computer 6d, thereby registering the properties of the clothes in the host computer 6d.

The data showing the properties of the new clothes in which the subject has just dressed can be also automatically registered in the computer 6d since the images of the new clothes can be distinguished from those of the bedclothes whose properties are known. In this case, however, it is necessary for the subject to change dresses at a designated position, or on the bed, not under the blanket to conceal the new clothes he or she is putting on.

Now the properties of the moving object, i.e. the subject, and the clothes he or she wears) and the properties of any other object in the sickroom have been detected and stored into the host computer 6d. Next, one of the above-mentioned three methods of detecting changes in the image of each designated portion can be performed, either singly or in combination, in the following four schemes, in order to determine whether or not the subject is walking in the sickroom.

Scheme 1 one of the three methods is used. The method, wherein the difference between consecutive two images is processed, is employed to detect the movement of the subject, when the background of the input image is bright and the clothes are dark or to the contrary when the background is dark and the clothes are bright. The method, wherein the RGB-density ratios of the pixels forming an image are compared with those of the pixels forming the preceding image, is employed to detect the movement of the subject, when the color of the background (e.g., cream color) of the input image much differs from the color of the clothes (e.g., red, blue, or green).

Scheme 2

One of the three methods is applied to each part of the background of the input image to detect the movement of the subject, when the background consists of parts having different properties.

Scheme 3

The three methods are used in combination. Whenever the difference obtained by any method is greater than a threshold value, it is determined that the subject moves. Alternatively, the results obtained by the three methods are appropriately weighted, and when the sum of the weighted results is greater than a threshold value, it is determined that the subject moves. The result obtained by the method which can detect the difference most easily and reliably is weighted most.

Scheme 4 The second method (comparison of hues) or the third method (comparison of creases) is first performed. If the movement of the subject cannot be detected from the result, both methods are performed, and the movement of the subject is determined from the results obtained by both methods.

In any of the four schemes described above, no information about the moving objects is utilized in the case where the result is not weighed in accordance with the part of the input image. The data-processing/control section 4 comprises a parallel computer. The parallel computer not only simultaneously process the data items output by the local modules, but also performs different tasks on the data representing a region of the input image. Hence, the parallel computer processes the data showing the input image, at high speed. The data-processing/control section 4 can perform scheme 3 with high efficiency. In scheme 3, the results obtained in the three methods can be weighted in accordance with the information about the moving objects, thereby enhancing the reliability of scheme 3.

In one case, less local modules are available than required to achieve scheme 3. In another case, an additional computer needs to be used to achieve scheme 3. In either case, the image data can be processed in accordance with the rules formulated from the relation between the properties of the moving objects, on the one hand, and the three methods of detecting changes in each designated portion of the image, on the other hand. As a result, the reliability of scheme 3 can be sufficiently high.

To detect more easily and economically whether or not the subject is walking in the sickroom, the subject must wear clothes of such properties that help to detect the changes in the designated portions with high accuracy. In this case, the subject's agreement to wear such clothes is required since he or she has preference to a specific color, a particular cut and a special material for his or her garment. To be more precise, the subject wears clothes which is in sharp contrast to the background objects (i.e., bedclothes, walls, floor, furniture, etc.). If the subject insists on wearing his or her favorite clothes which happen to be similar to the background objects, then the background objects need to be replaced, at the subject's expense, by new ones which are in complete contrast to the clothes the subject's has chosen. The word "contrast," used here, means a difference in brightness in the case where the fixed video camera 31b is a black-and-white one, and means a difference in color in the case where the camera 31b is a color video camera.

After changes are detected in the images of the designated portions, in step g2, the operation goes to step g3. In step g3, it is determined whether or not the changes are occurring in a large region. The term "large region" does not necessarily means a single large region only; it also means two or more small regions put together. Any region is considered "large" if it is larger than one of the several parts forming the smallest image of the subject that the fixed video camera 31b can photograph. That region of the input image which represents the subject's head which does move but slightly while the subject is sleeping in normal way is not regarded as one in which changes are taking place.

If NO in step g3, that is, if no changes are occurring in any large region of the input image, the operation moves to step g4, in which the video camera 31a built in the robot 5 is turned on, whereby step a5 is performed. In step g5, it is determined whether or not the subject is in bed. If YES, the operation returns to the main process, more precisely to step g1. If NO, the operation moves to step g14. In step g14, sub-process 1 is initiated, whereby it is detected whether or not the subject is walking in the sick room. If the subject is not moving in the sickroom, it is determined that the subject must be monitored and examined by a physician in the monitor room.

Sub-process 1 will be explained, with reference to the flow chart of FIG. 19B.

First, in step i1, the outlines of all objects in the sickroom, still ones and moving ones, are detected. The positions of the still objects are known. In step i2, the data items showing the positions of the moving objects (including the subject's head) are stored in the memories which have been reset and are thus empty. These data items have been obtained by extracting the video signals representing the pixels outside an enlarged outline image of each still object and then by enlarging the outline image defined by the pixels thus extracted.

Figure 9:
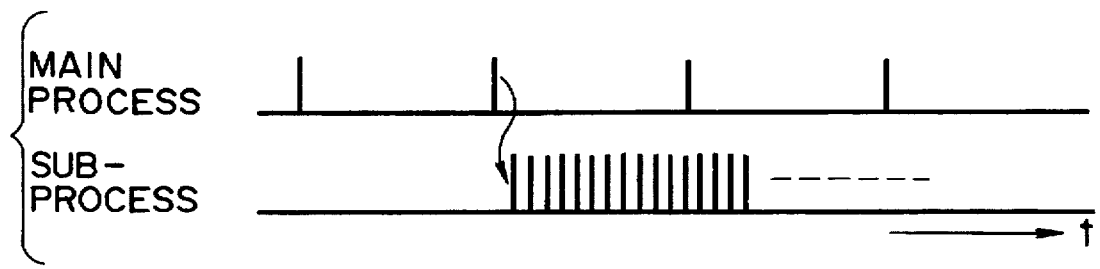
FIG. 9 is a timing chart representing the timing of inputting image data for the main process and sub-process performed by the image-processing apparatus.

Sub-process 1 is achieved by sampling the image data at short intervals as is shown in FIG. 9, by means of the signal processor 32. In step i3, it is determined whether or not a predetermined period has elapsed from the start of accumulating data items in each of the memories. If NO, the operation moves to step i4, in which the next image data is input to the processor 32. The processor 32 samples the next image data in step i1. If it is found, in step b1 of the main process, necessary to determine whether or not the subject is moving in the sickroom, the processor 32 samples each input image data at short intervals.

If YES in step i3, that is, if the predetermined period has elapsed from the time each memory starts accumulating data items, the operation moves to step i5. In step i5, it is determined whether or not the input image includes the image of an moving object. If NO, the operation goes to step i6, in which a signal is output which indicates that the image includes no moving objects. If YES in step is, the operation goes to step i7.

In step i7, it is determined whether or not any object is moving. This decision is made based on the ratio in number of the small-value pixels to the great-value pixels—all stored in the memories. More precisely, when this ratio is greater than a threshold value, it is determined that the input image includes the image of at least one moving object. This is be cause the pixels defining the outline of a movable object, if any in the input image, have great values when the outline does not move at all during said predetermined period. Hence, whether or not any object is moving can be determined very accurately.

If NO in step i7, that is, if no moving objects are detected in the input image, though there may be movable objects, the operation moves to step i8. In step i8, it is found necessary to monitor and examine the subject in the monitor room. If YES in step i7, that is, at least one object is found moving in the input image, the operation goes to step i9. In step i9, the memories are reset, whereby the data stored in them are erased. Thereafter, in step i10, the next image data is input to the signal processor 32.

If YES in step g3, that is, if changes taking place in a large region, the operation goes to step g6. In step g6, it is determined whether or not sub-process 2 is being performed. If YES, it is determined in step g7 whether or not the changes detected in step g3 contradict with the results of sub-process 2, which is the position of the subject's head in the input image as will be later described in detail. If NO in step g7, the operation moves to step g13, which sub-process 2 is started. If YES in step g7, that is, if the subject's head is not seen within the large region detected in step g3, the operation goes to step g8.

Figures 22A, 22B, 22C:
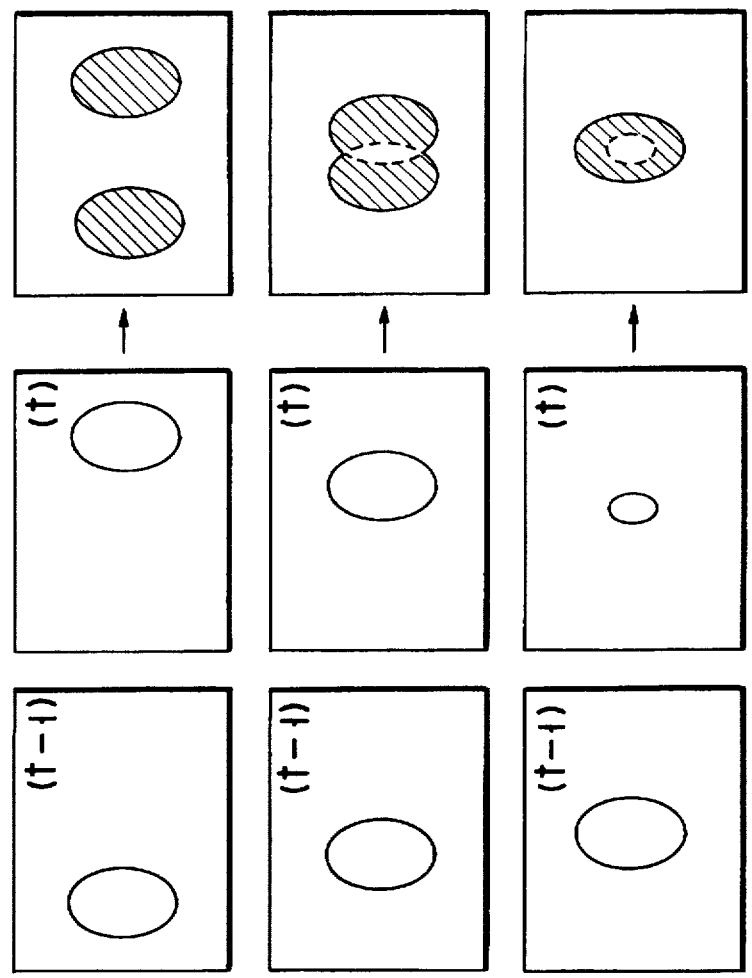
FIGS. 22A, 22B and 22C are diagrams, each representing the relation between the movement of an object and the shape of the image thereof.

In step g8, the size and shape of the large region are recognized, by distinguishing the region from the rest of the input image. Changes in the size and position of the large region indicate how the moving object moves with respect to the fixed video camera 31b. When the region moves in the input image as is shown in FIG. 22A, it means that the object moves from the right to the left with respect to the camera 31b. When the region moves as is shown in FIG. 22B, it means that the object moves from the right to the left, but for a shorter distance. When the size of the region decreases as is shown in FIG. 22C, it means that the object moves away from the fixed camera 31b.

As has been described, the data showing the region detected at time t-1 and the data showing the region detected at time t are stored into the same memory. Hence, the data stored in the memory represents two elliptical areas when the large region moves as is shown in FIG. 22A, represents two partly overlapping elliptical areas when the large region moves as is shown in FIG. 22B, and represents two completely overlapping elliptical areas, one larger than the other, when the large region moves away from the camera 31b as is shown in FIG. 22C. Not only the size of the large region, but also the shape thereof must be recognized since the shape also changes as the subject turns around, bend over, or moves his or her arms and legs.

Figure 24:
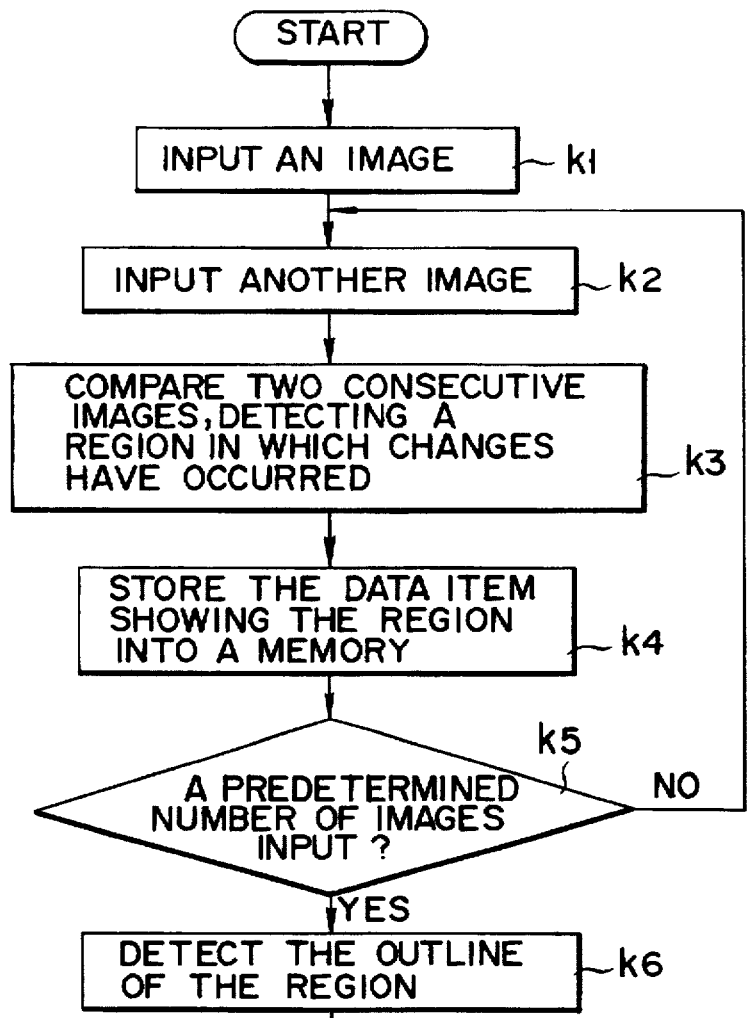
Figure 25:
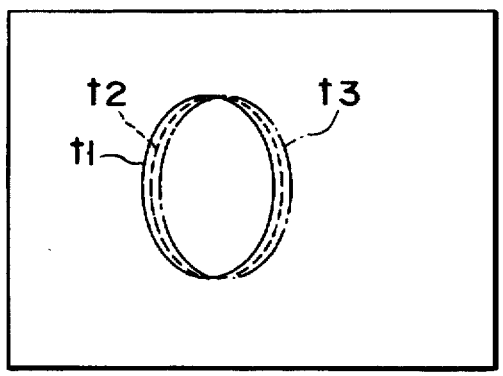
FIG. 25 is a diagram explaining the process of accumulating the data items showing the differences obtained in the object-extracting process.

There are two alternative methods of recognizing the size and shape of the large region detected in step g3. These methods will be explained, with reference to the flow charts of FIGS. 23 and 24.

In the first method, the region detected in step g3 is enlarged in step j1 by processing the video signals which are binary signals. Next, in step j2, the blank made as the result of the enlarging of the region is filled in. In step j3, the outline of the region of the image being formed is detected. Then, in step j4, the data items are erased from the memory, which represent the outlines of the regions detected previously. The data items showing outlines of the regions detected previously are erased, and the data item representing the outline of the region last detected in step g3 remains in the memory. Finally, in step j5, the size and shape of the moving object are recognized from the data kept stored in the memory.

In the second method of recognizing the size and shape of the large region, a first image is input to the signal processor 32 in step k1. Then, a second image is input to the processor 32 in step k2. In step k3, the first and second images are compared, thereby detecting a region in which changes have occurred. In step k4, the data item showing the region thus detected is stored into a memory. Then, in step k5, it is determined whether or not a predetermined number of input images have been processed. If NO, the operation returns to step k2, whereby steps k2, k3 and k4 are repeated. In this method, the images are input at so short intervals that they overlap each other as is shown in FIG. 22B. Hence, the data items accumulated in the memory represent the outlines of the region, detected at different times t1, t2, and t3. If YES in step k5, that is, the processor 32 has processed the predetermined number of images, the operation moves to step k6. In step k6, the outline of the region is detected from the data items accumulated in the memory.

After the size and shape of the large region are recognized in step g8, the operation moves to step g9. In step g9, it is determined whether or not any portion in the image seems to be the subject. More precisely, it is determined whether or not the size of the region, detected in step g8, falls within a specific range. If NO in step g9, the operation returns to step g4. If YES in step g9, it is determined that the subject is out of the bed, and the operation goes to step g10 and also to step g11.

In step g10, the subject's head is detected. More specifically, an arc portion, if any, of the outline of the region detected in step g3 is detected. Then, an elliptical region, defined in part by the arc portion, is regarded as representing the subject's head. Two or more arc portions of the outline may be detected. In this case, one or all of the elliptical regions partly defined by these arc portions, respectively, will be considered to represent the subject's head.

In the meantime, in step g11, sub-process 1 is stopped. This is because, if sub-process is performed at the time any portion in the image is identified with the subject in step g9, the subject is moving fast, and it is no longer necessary to input image data at short intervals to the signal processor 32. Then, in step g12, the memories are reset, erasing the data stored in them.

After the subject's head is detected in step g10, the operation goes to step g13, and sub-process 1 stopped in step g11, the operation goes to step g13. In step g13, sub-process 2 is started. Sub-process 2 will be explained in detail, with reference to the flow chart of FIG. 19C.

In sub-process 2, images are input to the signal processor 32 at short intervals in step m1. In step m2, the processor 32 processes the image data in order to detect the subject's head. This image data shows either a standard-exposure image or an image which the camera 31 has image-sensed in the exposure condition best for the subject's head. Then, in step m3, it is determined whether or not the processor 32 fails to detect the subject's head.

In the detection of the head in the sub-process 2, the detected head is used as a template, and this template is matched with the template corresponding to the peripheral portion of the head of the previous image, to obtain the portion on which the present template is completely matched with the previous template, and the position of the matched portion is decided as the present position of the head (step m2). For the above matching process may be used a correlation coefficient or the total sum of the absolute values of the differences between the intensities of the pixels. As the template may be used the information regarding to the head extracted at first or the template is updated by the head information detected for every time. Instead of the above matching process the position of the head may be decided by checking the peripheral pixels of the head of the present image and obtaining the outline of the head.

If the present position of the head cannot be detected by the peripheral portion of the previous head portion, in other word, the point having a larger coincident degree than a predetermined value is not detected, the operation goes to step m4, in which sub-process 2 is stopped. The subject's head is not detected, perhaps because the head has moved much. Nonetheless, sub-process 2 is performed since the great changes have been detected in step g3, and the position of the head is detected in step g10. Hence, there is no problem.

If NO in step m3, that is, if the subject's head is detected in step m3, the operation goes to step m5. In step m5, it is determined whether or not the head is moving. If NO, sub-process 1 is started in step m6. If YES, the operation returns to step m1, whereby steps m1, m2, and m3 are repeated.

In step i6, a signal may be output which indicates that the image includes no moving objects. This means that the signal-processing/control section 4 has failed to detect the subject. In this case, the section 4 outputs a message, either aural or visual, asking the subject to stand in front of the fixed video camera 31b. Alternatively, sub-process 1 is repeated a predetermined number of times, and the section 4 output the message only if a signal, which indicates that the image includes no moving objects, is output in step i6 of the sub-process 1 last performed.

In step i8, it may be found necessary to monitor and examine the subject in the monitor room. If this is the case, a signal indicating this fact is transmitted to the monitor section 2, whereby the physician in the monitor room can know that the subject needs to be monitored.

Not only through the processing of image data, but also by other means, can it be found necessary to monitor and examine the subject.

For instance, when an electrocardiograph, an electronic hemadynamometer, and an electronic thermometer are attached to the subject, it can be determined from the data output from these electronic devices that the subject must be monitored in the monitor room. In the case where the data reveals that the subject is in critical condition, the physician can operates the monitor console of the monitor section 2, thereby to examine the subject's image displayed on the CRT screen of the monitor console, without the subject's permission of the console.

When the subject pushes a button switch, utters a message, or makes a hand-signaling, informing the physician in the monitor room that he or she want the physician to examine him or her, then the physician operates the monitor console, and watches and examines the subject's image displayed on the CRT screen of the monitor console.

To examine the subject at a fixed time or times of the day, the physician pushes a button switch, thereby informing the subject that his or her image will be transmitted to the monitor section 2. Then, the physician operates the monitor console some time later, thereby examining the subject's image displayed on the CRT screen of the console.

When the data supplied from the data-processing/control section 4 to the monitor section 2 shows that the subject is sleeping, the physician can be authorized to operate the monitor console, thereby to monitor the subject and examine the subject's image on the CRT screen.

The subject can push a monitor-off button switch located within his reach, thereby suspending the examination whenever he or she finds it inconvenient to be examined continuously, as when his or her relative or friend comes into the sick room to see him. This button switch is automatically turned off upon lapse of a predetermined period, in accordance with the program installed in the data-processing/control section 4. Thus, the examination is started again even if the subject forgets to turn off the monitor-off button switch.

The monitoring of the subject can be automatically suspended when a visitor or a nurse comes into the sickroom. This can be accomplished by detecting the opening and closing of the door to the sickroom by means of a sensor, or by detecting the image of the visitor or nurse by means of the signal-processor 32 processing the image data output from the fixed video camera 31b. There is the possibility that the sensor and the processor 32 malfunction. Hence, whenever the opening or closing of the door, or the image of the visitor or nurse is detected, a message is given to the subject, asking whether the monitoring should be suspended or not. Unless the subject responds in affirmative, the monitoring is continued.

Needless to say, whenever it is found necessary to monitor the subject, the robot needs to ask the subject to permit the physician to monitor the subject. The request for permission can be conveyed to the subject by an aural message, a visual message, or a tactual message. The following aural, visual and tactual messages can be used, either singly or in combination.

a. Aural Message

A speech synthesizer generates speech signals. These signals are supplied to the speaker built in the robot 5 or the speaker located at bedside. The speaker converts the signals to an aural message such as "SHALL I ASK DR. SMITH TO EXAMINE YOU?" The speech synthesizer can generate speech signals, which the speaker converts to a message of "MOTHER, HOW ARE YOU FEELING NOW? SHALL I CALL DR. BROWN?" in a voice similar to that of the subject's daughter. Alternatively, the speech synthesizer can generates speech signals, which the speaker converts to a message of "GRANDMA, HOW ARE YOU? DO YOU WANT TO SEE DR. JONES?" in a voice almost the same as that of the subject's grandchild. Further, the speaker can give the subject similar synthesized aural messages in various voices.

b. Visual Message

Various visual messages can be given to the subject. For example, a message of several words can be displayed on the CRT screen on the robot 5. Instead, the ceiling lamp or the bedside lamp is made to flicker, asking the subject if he or she agrees to be monitored. Further, the arms of the robot 5 can be swung, asking the subject whether or not he or she wants the physician to examine him or her.

c. Tactual Message

The robot 5 can move its arms and hands, touching the bed or the subject, thus giving a tactual message asking the subject if he or she agrees to be monitored. Instead, the pillow or the bed can be vibrated by a vibrator, asking the subject whether or not he or she agrees to be monitored. Alternatively, a striker is actuated to hit the bed gently for the same purpose.

At night, the ceiling lamp or the bedside lamp is turned on shortly before a message, aural, visual or tactual, is given to the subject. If the subject does not hope that the room is illuminated, the message is given in the dark. In this case, the subject is expected to make an oral response or a tactual response, never a visual response which neither video camera 31a nor 31b can recognize in darkness. In the case where no response is required on the part of the subject, the sickroom is not illuminated, unless the subject wants to have the room lighted.

As has been described, the physician can operate the monitor console, thereby monitoring the subject, without the subject's permission, when the data output by the electronic sensors attached to the subject shows that the subject is in critical condition. Even in such a case, it is recommendable that a message, aural, visual or tactual, be given to the subject, informing the subject that the physician is about to start monitoring the subject.

After sending a message to the sickroom, asking the subject to permit the physician to monitor him or her, the physician waits for a response. If no response comes within a predetermined period of time, it is decided that there is something wrong with the subject, and hence operates the monitor console, and starts receiving the image data from the sickroom so that he or she can monitor the subject on the CRT screen.

The subject can make various types of responses to the aural, visual or tactual message given to him or her from the monitor room, asking him and her if he or she agrees to be monitored.

The easiest and most reliable response is pushing a button switch at bedside. The button switch should be of the type which can be operated not only by hand, but also by any other part of the patient. The subject pushes the switch only when he or she agrees to be monitored, or only when he or she disagrees to be monitored. Alternatively, two button switches are located at bedside so that the subject may push the first switch to express his or her approval, and the second switch to express his or her disapproval.

Another response is an oral or aural one. In response to the message given, the subject talks into the microphone mounted on the robot 5 or located at bedside, and his or her speech is recognized by the speech recognition device built in the robot 5, whereby the subject's approval or disapproval is conveyed to the physician. Instead, the subject clap hands or hits something near the robot 5, and the microphone picks up the resulting sound, which the robot hears to know the subject's approval or disapproval.

Another response is a visual one. The subject nods to show approval, or shakes his or her head to express disapproval. Alternatively, the subject makes a hand signaling, indicating approval or disapproval. These visual responses are detected by the video camera 31a built in the robot 5 or the video camera 31b installed in the sickroom and are conveyed to the robot through the data-processing/control section 4 which processes the video signals output from either camera and detects the movement of the subject's head and hands.

Not only a hand-signaling, but also nodding, shaking of the head, and facial expression can be visual responses. Nodding, head-shaking, and facial expression can be detected by performing the sub-process. The subject and the robot make an understanding between them that the subject turns his or her head toward the robot 5, expressing approval of being monitored, and does not do so, showing disapproval. A similar understanding can be made that the subject opens his or her mouth or eyes, indicating approval, and closes them, showing disapproval.

If the data-processing/control section 4 outputs, in step i6, a signal indicating that the image includes no moving objects, the same sequence of operations can be performed as in the case where it is determined, in step i8, that the physician should monitor and examine the subject. Alternatively, a message can be given to the subject, asking him or her to turn his or her head toward the robot 5 or to go back to the bed, so that the subject's image appears in the view field of the video camera 31a built in the robot 5. Once the subject accordingly turn the head toward the robot 5 or returns to the bed, changes occur in a region of the input image, whereby the subject's image can be detected.

If no changes occur in the region of the image input from the video camera 31a after a message is given to the subject, asking him or her to turn to the robot 5 or return to the bed, then the section 4 performs the same sequence of operations as in the case where it is determined, in step i8, that the physician should monitor and examine the subject. Before instructing the section 4 to carry out the sequence of operations, a message is given to the subject, asking for the consent that the subject is monitored. However, this message need not be given since the same message has once been given.

If the subject has pushed the button switch, making the most reliable response showing approval or disapproval of being monitored, it is unnecessary to confirm the subject's intention. Since an oral, aural or visual response the robot 5 detects may be false, a message should be given to confirm the subject's intention unless it is determined that the response is a true one.

Upon receipt of the subject's approval through the data-processing/control section 4, the monitor console automatically sends an aural, visual or tactual message to the subject, informing the subject that his or her image is about to be transmitted to the monitor section 2. At the same time, the lamp on the console flashes, and the CRT display also on the console displays a message, and the speaker built in the console gives a message, informing the physician that he or she must examine the subject's image sent from the data-acquiring section 1. Further, the monitor console can actuate the physician's pager, telling the physician to examine the subject's image in the monitor room.

The transmission of the subject's image to the monitor section 2 is started at the time the subject's approval reaches the monitor section 2, or at the time the physician pushes the transmission-start button on the monitor console. At the start of the image transmission, not at the time of receiving the subject's approval, the monitor console can send a message to the data-acquiring section 1, thus telling the subject that his or her image is being transmitted to the monitor section 2.

Now that the image transmission has begun, the physician looks at the subject's image displayed on the CRT screen on the monitor console. Whenever necessary, the physician switches the subject's image output by the video camera 31a built in the robot 5 to the one output by the fixed video camera 31b, and vice versa. Further, he or she operates the monitor console, thus adjusting the exposure condition of either camera, and moving the robot 5 and/or the camera built in the robot 5, in order to get a clearer image of the subject.

As has been described, the video camera installed in the monitor room, more precisely on the monitor console, outputs the data representing the physician's image, to the robot 5 through the signal transfer path 3, and the CRT display on the robot 5 displays the physician's image. Hence, the subject and the physician can talk, face to face, over the telephone or by means of microphones and speakers.

Since the video camera 31a built in the robot 5 does, so to speak, look down at the subject even if the robot's neck is contracted, it may be impossible to detect the subject's facial expression completely in the image the camera 31a outputs. To give the physician a better view of the subject's face, a video camera can be incorporated in the robot's trunk and be located right before the subject's face.

It is quite desirable that the subject be informed of the transmission of his or her image to the monitor section 2, not only immediately before or at the start of the image transmission, but also during the image transmission. Therefore, in the present embodiment, the CRT display mounted on the robot 5 displays exactly the same image as the CRT display mounted on the monitor console displays and as the physician sees. Hence, the subject can know in which way he or she is being monitored by the physician.

The monitor section 2 comprises an apparatus for recording the images being monitored in the monitor room, in the following various ways:

(a) To record the input image at regular intervals, each time for a short period.

(b) To record the input image for a predetermined period, starting at the time greater changes are detected in the image.

(c) To record the input image, starting at the time no moving objects are detected in the image or it is found necessary to monitor the subject, until the physician begins to examine the subject's image or finds it no longer necessary to examine the subject's image.

(d) To record the input image continuously, but automatically erase the image data acquired until about ten and odd minutes ago. Hence, the physician can review the subject's image recorded for that ten-and-odd minutes period and can copy the the recorded image on other video tape, whenever no moving objects are detected in the image or whenever it is found necessary to monitor the subject.

As is shown in FIG. 26, the recording apparatus comprises a long-time video recorder 11, a short-time video recorder 12, a long-time recording controller 13, a short-time recording controller 14, a timer section 15, and a reply-agreement judging section 16. The video signals and, if necessary, the audio signals, output by the video cameras 31a and 31b are input to both video recorders 11 and 12. The signal indicating that the subject must be monitored, and the signal indicating that no moving objects are found, both output from the data-processing/control section 4, are supplied to both recording controllers 13 and 14. Further, the signal showing that changes are occurring in the input image is input to the long-time recording controller 13, and the physician's instructions are supplied to both recording controllers 13 and 14.

The timer section 15 outputs timer signals at predetermined intervals, each timer signal having a predetermined duration, and supplies them to the long-time recording controller 13. Under the control of these timer signals, the controller 13 are turned on and off, whereby the intermittent image-recording defined in paragraph (a). Upon receipt of the signal showing that changes are occurring in the input image, the controller 13 causes the long-time video recorder 11 to start recording the input image, whereby the image-recording of the type defined in paragraph (b) is carried out. Upon receipt of the signal indicating that the subject must be monitored, or the signal showing that no moving objects are found, the section 13 causes the video recorder 11 to start recording the input image, whereby the image-recording of the type defined in paragraph (d) is accomplished.

The long-time video recorder 11 starts recording the input image at the time an image-transmission start signal is supplied to the long-time recording controller 13. The video recorder 11 stops recording the input image upon lapse of a predetermined period or at the time it receives a recording stop signal from the monitor console. Thus, once the controller 13 has received the signal showing that the subject must be monitored, the signal indicating that no moving objects are found, or the signal showing that changes are occurring in the input image, the long-time video recorder 11 keeps recording the input image until it receives the recording stop signal from the monitor console.

The short-time video recorder 12 records the input image at all times, and automatically erases the image recorded for the previous ten minutes. This can be achieved by the use of an video tape which is long enough to record image data for about a ten minute period, or by the use to two recording units. In the first case, the video tape long enough to record image data for about a ten minute period is run continuously, so that new image data is over written on the old image data. In the second case, the first recorder unit starts recording image data when the second recorder unit finishes recording the input image for about ten minutes, and the second recorder unit erases the recorded data while the first recorder unit is recording image data.

Upon receipt of the signal showing that the subject must be monitored and the signal indicating that no moving objects are found, the short-time recording controller 14 causes the short-time video recorder 12 to supply the image data recorded for the last ten minutes or so, to the long-time video recorder 11. In this case, the long-time video recorder 11 records that image data.

According to the invention, only one video recorder can be used to record, in time-division fashion, the image data items output by the two video cameras 31a and 31b. Alternatively, two video recorders can be used to record the image data items supplied from the two video cameras 31a and 31b, respectively.

Moreover, a data item showing the image-recording time and a data item showing the results of image-processing can be recorded as attribute data items on the video tape, together with the image data.

It is desirable that the physician should obtain the subject's consent before reproducing the subject's image from the recorded video tape. The replay-agreement judging section 16 determines whether or not the subject agrees that the image should be reproduced from the tape. The physician turns on this section 19 when he or she wishes to get the recorded image reproduced. Then, the section 16 gives an aural, visual or tactual message to the subject, asking whether or not the subject agrees on the reproduction of his or her recorded image. The data-processing/control section 4 detects the the approval or disapproval the subject makes, and transmits the data representing the approval or disapproval to the replay-agreement judging section 16. From this data does the section 16 determine the subject's agreement or disagreement as to the reproduction of his or her recorded image. Needless to say, the physician can directly ask the subject, either over the telephone or by means of the microphone-speaker system, whether or not the subject agrees on the reproduction of the recorded image. If the subject's consent to the reproduction of recorded image has already been obtained before the transmission of the image data to the monitor section 2, the replay-agreement judging section 16 need not be operated at all.

It is also desirable that the subject's image be reproduced from the tape and be displayed on the CRT screen on the robot 5, not on any CRT screen on the monitor console, so that only the subject can see the reproduced his or her own image. In this case, only if the subject agrees that the image is reproduced and displayed on the CRT screen of the monitor console, the physician can examine the image reproduced from the recorded video tape.

As can be understood from FIG. 4, the robot's nose is the zoom-lens cylinder of the video camera is built in the robot's head. Three drive mechanisms 5a, 5b and 5c are incorporated in the neck of the robot 5. The mechanism 5a turns the robot's head to the left and the right. The mechanism 5b bends the robot's head forward and backward. The mechanism 5c moves the robot's head up and down. Another drive mechanism is incorporated in the trunk of the robot 5. When this mechanism is actuated, the robot 5 moves in any direction on the floor.

The drive mechanisms incorporated in the robot 5 are remote-controlled by operating the monitor console of the monitor section 2. Thus, under the control of the monitor section 2, the robot 5 is moved to a desired position with respect to the subject, and its head is turned, bent and vertically moved until its nose (i.e., the zoom-lens cylinder) is directed to the subject's face. When the subject walks in the sickroom, the robot's head is moved, thus tracking the subject so that the subject's image remains in the view field of the video camera.

Since the greater part of the video camera is concealed in the robot's head, the subject is less conscious of being monitored than in the case where the camera is exposed in its entirety. Hence, the robot 5 is friendly to the subject, not only because it can talk due to the use of the speech recognizer and the speech synthesizer.

As has been explained, whenever the subject does not move or bears strange facial expression, it is found necessary to monitor and examine the subject, and the monitor section 2 gives the subject a message asking whether or not the subject agrees to be monitored. The robot 5 can give the message, aural or written, like "HELLO, MR. BAUM. HOW ARE YOU FEELING NOW?," not only on such an occasion, but also at long intervals, in order to cheer up the subject, unless the subject does not want to hear or see such repeated messages.

The robot 5 can have a language analyzer which analyzes the subject's spoken words detected by the speech recognizer, and generates speech signals representing suitable verbal responses. The speech synthesizer converts these signals into aural responses, which the subject can understand. In this case, the robot 5 is more friendly to the subject.

The language analyzer, which is an expensive device, can be replaced with a tape recorder having a roll of recorded tape from which chime-in words such as "Yes," and "I see" can be reproduced whenever the speech recognizer detects a pause in the subject's talk.

The CRT display on the robot 5 can be used as an ordinary TV receiver. Hence, the subject can enjoy seeing any TV program he or she likes to. Also, the telephone integrated with the robot 5 can be connected to telephones outside the hospital, enabling the subject to make calls to relatives and friends and to receive calls from them. The robot 5 is, therefore, more friendly and helpful than otherwise.

The robot 5 incorporates other drive mechanisms for driving the robot's arms and hands. Therefore, the robot 5 can serve the subject a glass of water, can help the subject to have meal, and can hold a book for the subject.

The robot 5 shown in FIG. 4 can be replaced by a wheelchair robot of the type shown in FIG. 27, in case the subject is unable to walk. If the subject cannot set up by himself or herself, the robot's arm can be made tough enough to help the subject rise up from the bed. Also, if necessary, the robot's arm can be so designed as to hold and lift the subject off the bed.

The robot 5 is connected to the local station in the sick room. It can be disconnected from the local station so that it can walk more freely in the sick room, by remote control. The physician in the monitor room can instead remote-control the robot 5 in accordance with the image sent from the video camera 31. How ever, this image alone is insufficient for the physician to know the position the robot 5 assumes with respect to other objects existing in the sickroom. To guide the robot 5, preventing collision between the robot 5 and any other object in the room, the physician sees not only the image photographed by the camera 31a in the robot 5, but also the image output by the fixed video camera 31b and showing not only the robot 5 but also the other objects. Further, by seeing the images output by both video cameras 31a and 31b, the physician can well control the robot 5 to move the arms and hand thereof since he or she can perceive the position relation between the object (possibly the subject) which the robot's arms and hands are to hold, on the one hand, and other objects, on the other.

To help the physician to control the robot 5 more accurately, the camera 31a built in the robot 5 can be replaced by a so-called stereoscopic video camera, and the fixed video camera 31b can also be replaced by a stereoscopic video camera. The 3-dimensional images output by these cameras indicate the position relation between the objects (including the subject) more precisely than 2-dimensional images.

The remote control and self-control of the robot 5 will now be described in detail. As is shown in FIG. 28, an infrared-ray emitting diode is mounted on the top of the robot's head. The robot 5 has height h unless its head is bent forwards or backwards. The fixed video camera 31b has a fixed position, just as its name suggests. More specifically, the camera 31b is at level H above the floor, and its optical axis is at angle $\alpha$ to the vertical line. Let us assume that an angle $\theta$ is defined between the optical axis of the camera and the line passing the center of the zoom lens 31b of the camera 31b and the infrared-ray emitting diode. Then, the distance x from the infrared-ray emitting diode to the center of the zoom lens as projected on the vertical plane in which the diode exists is calculated as follows:

$$x = (H-h) \tan(\alpha+\theta) \quad (1)$$

Then, the distance y from the diode to the center of the zoom lens as projected on the horizontal plane in which diode exists is found by similar calculation. As a result, the position the diode takes in that horizontal plane is determined.

It is desirable that the diode be located on the top of the robot's head and in the vertical line passing the horizontal axis around which the robot's head is bend forwards or backwards. Were the diode located off that vertical line, the robot's height h should change as the robot's head is bent forwards or backwards. If this change in the height h is negligible, not influencing the calculation of equation (1), the diode can be located at any position on the top of the robot's head.

To detect in which way the robot's head is turned, it is required that two or more infrared-ray emitting diodes be arranged as is shown in FIG. 29. Namely, these diodes should be arranged in the line which is parallel to, and exists in the same vertical plane as, the horizontal axis around which the robot's head is bend forwards or backwards.

How the robot 5 is guided to a desired position will now be explained. First, the position of the infrared-ray emitting diode is determined, by the calculation of equation (1). A mark indicating the position of the diode is displayed in the image output by the fixed video camera 31b. Then, the physician operates the monitor console, thus displaying in the image another mark which indicates the desired position. Next, he or she operates the monitor console, control ling the drive mechanism incorporated in the robot 5 and designed to propel the robot 5, whereby the robot 5 starts walking. As the robot 6 walks by remote control, the angle $\theta$ changes. The calculation of equation (1) is repeated at predetermined intervals, thus determining the present position of the infrared-ray emitting diode. The mark indicating the position of the diode moves in the image accordingly. The physician continues to control the robot-propelling mechanism such that the mark does not touch the image of any object in the sickroom. He or she keeps controlling the mechanism until the mark reaches the mark representing the desired position.

The robot 5 has several ultrasonic sensors on its trunk. The ultrasonic sensors detect the distances between the robot 5 and the other objects in the sick room. An alarm signal is generated and transmitted to the monitor section 2 when any ultrasonic sensor detects that the robot 5 is too close to any other object. The monitor console converts this signal into a visual or aural alarm, telling the physician to take care not to make the robot hit the object.

Two or more fixed video camera can be installed at different positions in the sickroom, so that the physician can see the image of every part of the room on the CRT mounted on the monitor console. This enables the physician to guide the robot 5 to the desired position, more easily and more precisely.

The robot 5 can self-control as well as the physician can guide the robot 5, determining the position of the robot 5 from the image output by the camera 31a built in the robot 5, not from the image output by the fixed video camera 31b. In this case, it is desirable that marks are pasted on the floor and walls of the sickroom, whereby these marks appearing in the image output by the robot's camera helps the physician to determine the position of the robot 5, more easily and correctly. Alternatively, signal lines can be laid on the floor, along the route the robot 5 should walk to the desired position, so that the physician may control the robot-propelling mechanism in accordance with the intensity of the magnetic field the signal line is generating.

The wheelchair robot shown in FIG. 27 can have various sensors to achieve self-control, instead of remote control. The signals output by these sensors and the data obtained by processing the image data output by the robot's video camera and representing the position of the robot 5 control the drive mechanisms. Thus controlled, the drive mechanisms cause the robot 5 to walk and move its arms and hands. If this is the case, the wheelchair robot can take the subject from room to room on the same floor.

An additional video camera can be incorporated in the robot 5, for example in the robot's trunk, so that the physician can see a better view of the subject's facial expression. This is because the camera 31a built in the robot's head usually is positioned higher than the subject's head, looking down at the subject's face and, hence, failing to provide a complete image of the subject's face.

If two or more fixed video cameras are used in the sickroom, it suffices to process the video signals output by one of these cameras which provides the largest image of the subject's head, which shows the best view of the subject's face. As soon as the image of the subject's head disappears from the image output from this video camera, the video signals output from any other camera which provides the largest image of the head are processed. As a result, the physician can have the best possible image of the subject's face displayed on the CRT screen on the monitor console.

No fixed video camera is required if the subject's image output by the video camera built in the robot's head and the data items detected by the sensors attached to the robot 5 are sufficient for the physician to guide the robot 5 to a desired position in the sick room. Without fixed video cameras, the monitor system can be simple in structure.

Although the robot 5 is useful as has been described, it can be dispensed with if a fixed video camera suffices to monitor the subject. If no robot is employed, however, a CRT display, a microphone, a speaker, a button switch, and the like must be arranged near the bed. Otherwise, the subject and the physician in the monitor room cannot communicate with each other. It is therefore necessary to integrate these devices into a single unit which looks like a robot. In this case, two or more fixed video cameras are installed in the sickroom, if necessary. Each camera should better equipped with a zoom lens so that the subject's image can be enlarged to enable the physician to examine the subject's facial expression, or the image of the sick room can be enlarged to enables the physician to track the subject walking in the room.

The fixed video camera 31b can be connected to the wall or ceiling by means of a swivel, so that it can move around to scan almost every part of the room.

Then, no additional fixed cameras are required, or only a few additional fixed cameras are sufficient.

In the embodiment described above, the exposure condition of either video camera is changed at regular intervals in order to detect a moving object, if any, in the image input from the camera. Two cameras, a fixed camera and a camera built in the robot 5, are sufficient since no objects in the sickroom (including the subject) are supposed to move fast. It should be noted that what the physician must examine is slow and slight movement of the subject to determine the subject's condition. In most cases it suffices to change the exposure condition of either camera at regular intervals.

Nonetheless, a plurality of video cameras can be used and operated in different exposure conditions, scanning the same object at the same time, so that objects moving fast, as well as those moving slowly, can be detected. Here arises a problem, however. Since the cameras cannot take the identical position, the images of the same object they form are not completely identical in size and shape. To avoid this problem, the video camera of the type shown in FIG. 30 can be employed in the monitor system of the present invention.

As is shown in FIG. 30, the video camera comprises a lens 21, a prism system or an optical system 22, three charge-coupled devices (CCDs) 23a, 23b and 23c, three ND filters 24a, 24b and 24c, and a diaphragm 25. The system 22 has two half-mirrors and two reflectors. The CCDs 23a to 23c are located at the output side of the prism 22. The ND filters 24a to 24c are interposed between the prism 22 and the CCDs 23a, 23b and 23c. The filters 24a, 24b and 24c have different transmittances, i.e., high, intermediate and transmittances, respectively. The ND filter 24a having high transmittance can be dispensed with.

In operation, the light from an object is applied to the lens 21. The diaphragm 25 controls the amount of light passing through the lens 21. The light output from the lens 21 is applied to the optical system 22. In the system 22, the first half-mirror splits the light into two beams. The first beam is reflected by the first reflector and applied to the CCD 23c through the ND filter 24c. The second half-mirror splits the second beam into two beams, one of which is reflected by the second reflector and applied to the CCD 23a via the ND filter 24a, and the other of which is applied to the CCD 23b through the ND filter 24b.

The diaphragm 25 controls the amount of light to such a value that the CCD 23b forms a standard-exposure image from the beam passing through the ND filter 24b which have the intermediate transmittance. The CCD 23a forms an over-exposure image since it receives the beam passing through the ND filter 24a which has high transmittance. The CCD 23c forms an under-exposure image since it receives the beam passing through the ND filter 24c which has low transmittance. The CCDs 23a, 23b, and 23c form three images substantially at the same time, which are perfectly identical in size and shape, though different in exposure.

The ND filters 24a, 24b, and 24c are be monochroic ones. Alternatively, they are a red filter, a green filter and a blue filter, respectively. The CCDs 23a, 23b, and 23c form identical images of different densities in the first case, and three identical images of different colors.

The ND filters 24a, 24b, and 24c can be mounted on the output surface of the optical system 22, instead of being interposed between the system 22 and the CCDs 23a, 23b and 23c. The ND filters can be dispensed with, in which case the half-mirrors and reflectors of the optical system 22 must have different transmittances and different reflectances.

As has just been explained, one of the two alter native methods can be employed in the present invention to form images of different exposures. The first method is to use a single camera and change the exposure condition thereof in time-division fashion. The second method is to use two or more photographing means and operate them under different exposure conditions. Nevertheless, both methods can be applied in combination, whereby the exposure condition of each photographing means is changed at intervals, thus forming more images of various exposures.

As has been explained, in the monitor system of the invention, the image data output by either video camera is transmitted to the monitor section 2 after the subject agrees to be monitored. In other words, the subject's image can be displayed in the monitor room only when the subject approves the monitoring of his or her image. Therefore, the monitor system neither invades the subject's privacy nor makes the subject conscious of being watched. Moreover, an alarm is transmitted to from the data-processing/control section 4 to the monitor section 2 whenever it is determined that the subject is in critical condition, physicians is relieved from the duty of watching the subject for a long time.

What is claimed is:

1. A patient monitoring system comprising:
   patient data acquiring means, located within a hospital sickroom where a patient exists, for acquiring patient image data including an image of the patient, said patient data acquiring means an image pick-up device for outputting the patient image data corresponding to the image;

means for detecting facial outline of the patient on the basis of the patient image data;

means for determining facial feature candidate regions on the basis of at least the facial outline;

means for processing image data corresponding to each of the facial feature candidate regions, to detect some facial features of the patient;

means for checking a difference between a real-time facial pattern formed of the detected facial features and a facial pattern indicating an normal state and for detecting frequent appearance of strange expressions represented by the real-time facial pattern to output critical state information;

display means, located within a monitor room separate from said hospital sickroom, including a display monitor for displaying said image of said patient; and data transmitting means, located within said hospital sickroom, for transmitting said patient image data acquired by said image pick-up device to said display means in response to the critical state information to permit the physician examine the medical condition of the patient.

2. The patient monitoring system according to claim 1, further comprising informing means, located within said hospital sickroom, for informing said patient that transmission of said patient data to said display means via said data transmitting means has been inhibited for time periods during which said transmission of said patient data has been inhibited.

3. The patient monitoring system according to claim 2, wherein said informing means includes at least one of a signal lamp, a sound speaker, and display means for conveying to said patient that transmission of said patient data is inhibited.

4. The patient monitoring system according to claim 1, wherein said data transmitting means includes means for transmitting said patient data to said display means when said detecting means has not determined whether or not an examination of said medical condition of said patient by a physician is necessary within a predetermined amount of time measured from a beginning of such a determining operation.

5. The patient monitoring system according to claim 1, wherein said processing means include means for detecting a mouth, a nose, eyes and eyebrows as the facial features from the facial feature candidate regions.

6. The patient monitoring system according to claim 5, wherein said means checking means include means for for comparing the detected facial pattern formed of the detected facial features with a stable facial pattern corresponding to a stable condition of the patient and output the critical patient information in accordance with a difference between the detected facial pattern and the stable facial pattern.

7. The patient monitoring system according to claim 1, wherein said processing means comprises a plurality of local modules for processing image data corresponding to the facial feature candidate regions, respectively, and outputting data representing the facial features.

8. A patient monitoring system comprising:

patient data acquiring means, located within a hospital sickroom where a patient exists, for acquiring patient image data including an image of said patient, said patient data acquiring means including an image pick-up device for outputting the patient image data corresponding to the image;

means for detecting a facial outline of the patient on the basis of the patient image data;

means for determining facial feature candidate regions on the basis of the facial outline;

means for processing image data corresponding to each of the facial feature candidate regions, to detect some facial features of the patient;

means for checking a difference between a real-time facial pattern formed of the detected facial features and a facial pattern indicating an normal state and for detecting frequent appearance of strange expressions represented by the real-time facial pattern to output critical state information;

message transmitting means for transmitting a message from said patient data acquiring means to said patient in response to the critical state information, said message requesting permission from said patient for an examination of said medical condition of said patient by a physician when said detecting means determined that such an examination is necessary;

agreement-recognizing means, provided within said patient data acquiring means, for detecting an agreement by said patient to undergo an examination of said medical condition of said patient by a physician;

display means, located within a monitor room separate from said hospital sickroom, including a data receiving means for receiving said patient data acquiring means, and a display monitor for displaying said image of said patient; and data transmitting means, located within said hospital sickroom, for transmitting said image of said patient acquired by said patient data acquiring means to said display means only when said detecting means determines that an examination of said medical condition of said patient is necessary so that a physician in said monitor room can examine said medical condition of said patient by viewing said image of said patient on said display monitor only when said detecting means determines that an examination of said medical condition of said patient is necessary.

9. The patient monitoring system according to claim 8, wherein said detecting means includes means for detecting changes in said patient's facial expression by detecting changes in said image of said patient over time.

10. The patient monitoring system according to claim 8, wherein said detecting means includes means for determining whether or not it is necessary for a physician to examine said medical condition of said patient on the basis of said patient data acquired via said patient data acquiring means.

11. The patient monitoring system according to claim 8, wherein said detecting means includes means for detecting changes in said patient's facial expression by detecting changes in said image of said patient over time, and means for detecting whether or not said patient agrees to undergo an examination of said medical condition of said patient by a physician on the basis of said changes detected in said patient's facial expression.

12. The patient monitoring system according to claim 8, wherein said patient data acquiring means includes a robot to which a first video camera is attached for photographing said patient.

13. The patient monitoring system according to claim 12, wherein said patient data acquiring means further includes a second video camera for photographing said patient and said background of said patient.

14. The patient monitoring system according to claim 12, wherein said patient data acquiring means further includes electronic medical diagnosis means located in said hospital sickroom for outputting said diagnostic data relating to said medical condition of said patient.

15. The patient monitoring system according to claim 8, wherein said patient data acquiring means includes a robot which is moveable within said hospital sickroom, and wherein said message transmitting means includes at least one of the following:

display means attached to said robot for transmitting said message to said patient in visual format, and speaker means attached to said robot for transmitting said message to said patient in aural format.

16. The patient monitoring system according to claim 8, wherein agreement-recognizing means determines that said patient has agreed to undergo an examination of said medical condition of said patient by a physician when said patient has not responded to said message transmitted by said message transmitting means within a predetermined amount of time.

17. A patient monitoring system comprising:

patient data acquiring means, located within a hospital sickroom where a patient exists, for acquiring patient image data including an image of said patient, said patient data acquiring means including an image pick-up device for outputting the patient image data corresponding to the image;

means for detecting a facial outline of the patient on the basis of the patient image data;

means for determining facial feature candidate regions on the basis of the facial outline;

means for processing image data corresponding to each of the facial feature candidate regions, to detect some facial features of the patient;

means for checking a difference between a real-time facial pattern formed of the detected facial features and a facial pattern indicating an normal state and for detecting frequent appearance of strange expressions represented the real-time facial pattern to output critical state information;

message transmitting means for transmitting a message from said patient data acquiring means to said patient in response to the critical state information, said message requesting permission from said patient for an examination of said medical condition of said patient by a physician;

response detecting means for determining said patient's response to said message;

display means, located within a monitor room separate from said hospital sickroom, including a display monitor for displaying said image of said patient; and data transmitting means, located within said hospital sickroom, for transmitting said image of said patient to said display means only when said detecting means has detected that said patient has agreed to undergo an examination of said medical condition of said patient so that a physician in said monitor room can examine said patients medical condition by viewing said image of said patient on said display monitor only when said response detecting means has agreed to undergo such an examination by said physician.

18. A method for monitoring a patient comprising the steps of:

generating patient image data including an image of a patient;

detecting a facial outline of the patient on the basis of the patient image data;

determining facial feature candidate regions on the basis of at least the facial outline;

processing image data corresponding to each of the facial feature candidate regions, to detect some facial features of the patient;

checking a difference between a real-time facial pattern formed of the detected facial features and a facial pattern detecting frequent appearance of strange expressions represents the real-time facial pattern to output critical state information;

transmitting said image of said patient to display means in response to the critical state information to permit the physician examine the medical condition of the patient.

* * * * *